US012496215B2

(12) United States Patent
Canary et al.

(10) Patent No.: US 12,496,215 B2
(45) Date of Patent: Dec. 16, 2025

(54) TRANSPARENT PAD

(71) Applicant: C. R. Bard, Inc., Franklin Lakes, NJ (US)

(72) Inventors: Cecille A. Canary, Atlanta, GA (US); Nathaniel Barnes, Covington, GA (US); Christopher K. Brooks, Lawrenceville, GA (US); Younggeun Cho, Covington, GA (US); Sean E. Walker, Platteville, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 754 days.

(21) Appl. No.: 17/583,090

(22) Filed: Jan. 24, 2022

(65) Prior Publication Data

US 2022/0233347 A1 Jul. 28, 2022

Related U.S. Application Data

(60) Provisional application No. 63/141,358, filed on Jan. 25, 2021.

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0054* (2013.01); *A61F 2007/0247* (2013.01)

(58) Field of Classification Search
CPC ............................................... A61F 2007/0054
See application file for complete search history.

(56) References Cited

U.S. PATENT DOCUMENTS

| | | | |
|---|---|---|---|
| 2,167,865 | A | 8/1939 | Beecher |
| 2,250,325 | A | 7/1941 | Barnes |
| 2,296,207 | A | 9/1942 | Kittinger |
| 2,595,328 | A | 5/1952 | Bowen |
| 2,602,302 | A | 7/1952 | Poux |
| 2,726,658 | A | 12/1955 | Chessey |
| 2,807,809 | A | 10/1957 | Kottemann |

(Continued)

FOREIGN PATENT DOCUMENTS

| | | | |
|---|---|---|---|
| AU | 678753 | B3 | 6/1997 |
| AU | 2007201161 | B2 | 12/2010 |

(Continued)

OTHER PUBLICATIONS

English Translation of KR 2011 0020420A (Year: 2011).*

(Continued)

*Primary Examiner* — Kaitlyn E Smith
(74) *Attorney, Agent, or Firm* — Rutan & Tucker LLP

(57) ABSTRACT

Disclosed herein is a medical pad for exchanging thermal energy between a targeted temperature management (TTM) fluid and a patient. The pad includes a top side and a bottom side, as well as a fluid containing layer disposed between the top side and the bottom side, an insulation layer disposed on the top side, and a thermal conduction layer disposed on the bottom side. The pad can be configured to inhibit irritation of the skin of the patient when the pad is applied to the skin. The pad can also include translucent portions to facilitate visual observance of the skin beneath the pad.

5 Claims, 10 Drawing Sheets

(56) References Cited

U.S. PATENT DOCUMENTS

| | | | |
|---|---|---|---|
| 3,075,529 | A | 1/1963 | Young, Jr. |
| 3,091,242 | A | 5/1963 | Johnson, Jr. et al. |
| 3,212,286 | A | 10/1965 | Curtis |
| 3,506,013 | A | 4/1970 | Zdenek |
| 3,734,293 | A | 5/1973 | Biskis |
| 3,830,676 | A | 8/1974 | Elkins |
| 3,867,939 | A | 2/1975 | Moore et al. |
| 3,900,035 | A | 8/1975 | Welch et al. |
| 3,927,671 | A | 12/1975 | Chittenden et al. |
| 3,945,617 | A | 3/1976 | Callery |
| 3,995,621 | A | 12/1976 | Fletcher et al. |
| 4,059,293 | A | 11/1977 | Sipler |
| 4,092,982 | A | 6/1978 | Salem |
| 4,108,146 | A | 8/1978 | Golden |
| 4,114,620 | A | 9/1978 | Moore et al. |
| 4,118,946 | A | 10/1978 | Tubin |
| 4,149,541 | A | 4/1979 | Gammons et al. |
| 4,154,245 | A | 5/1979 | Daily |
| 4,161,210 | A | 7/1979 | Reid et al. |
| 4,195,631 | A | 4/1980 | Baucom |
| 4,311,022 | A | 1/1982 | Hall |
| 4,444,727 | A | 4/1984 | Yanagihara et al. |
| 4,508,123 | A | 4/1985 | Wyatt et al. |
| 4,580,408 | A | 4/1986 | Stuebner |
| 4,753,241 | A | 6/1988 | Brannigan et al. |
| 4,834,705 | A | 5/1989 | Vaillancourt |
| 4,846,176 | A | 7/1989 | Golden |
| 4,867,748 | A | 9/1989 | Samuelsen |
| 4,884,304 | A | 12/1989 | Elkins |
| 4,886,063 | A | 12/1989 | Crews |
| 4,908,248 | A | 3/1990 | Nakashima et al. |
| 4,919,134 | A | 4/1990 | Streeter |
| 4,962,761 | A | 10/1990 | Golden |
| 4,971,056 | A | 11/1990 | Seacord |
| 4,981,135 | A | 1/1991 | Hardy |
| 4,989,607 | A | 2/1991 | Keusch et al. |
| 5,000,252 | A | 3/1991 | Faghri |
| 5,005,374 | A | 4/1991 | Spitler |
| 5,050,596 | A | 9/1991 | Walasek et al. |
| 5,062,414 | A | 11/1991 | Grim |
| 5,072,875 | A | 12/1991 | Zacoi |
| 5,090,409 | A | 2/1992 | Genis |
| 5,097,829 | A | 3/1992 | Quisenberry |
| 5,111,668 | A | 5/1992 | Parrish et al. |
| 5,113,666 | A | 5/1992 | Parrish et al. |
| 5,133,348 | A | 7/1992 | Mayn |
| 5,146,625 | A | 9/1992 | Steele et al. |
| 5,154,706 | A | 10/1992 | Cartmell et al. |
| 5,190,032 | A | 3/1993 | Zacoi |
| 5,265,669 | A | 11/1993 | Schneider |
| 5,268,022 | A | 12/1993 | Garrett et al. |
| 5,289,695 | A | 3/1994 | Parrish et al. |
| 5,300,103 | A | 4/1994 | Stempel et al. |
| 5,304,213 | A | 4/1994 | Berke et al. |
| 5,304,216 | A | 4/1994 | Wallace |
| 5,320,164 | A | 6/1994 | Szczesuil et al. |
| 5,383,919 | A | 1/1995 | Kelly et al. |
| 5,393,462 | A | 2/1995 | Avery |
| 5,405,366 | A | 4/1995 | Fox et al. |
| 5,407,421 | A | 4/1995 | Goldsmith |
| 5,409,500 | A | 4/1995 | Dyrek |
| 5,411,541 | A | 5/1995 | Bell et al. |
| 5,423,751 | A | 6/1995 | Harrison et al. |
| 5,431,622 | A | 7/1995 | Pyrozyk et al. |
| 5,456,701 | A | 10/1995 | Stout |
| 5,466,250 | A | 11/1995 | Johnson, Jr. et al. |
| 5,470,353 | A | 11/1995 | Jensen |
| 5,476,489 | A | 12/1995 | Koewler |
| 5,484,448 | A | 1/1996 | Steele et al. |
| 5,486,207 | A | 1/1996 | Mahawili |
| 5,514,169 | A | 5/1996 | Dickerhoff et al. |
| 5,545,194 | A | 8/1996 | Augustine |
| 5,566,413 | A | 10/1996 | Webb et al. |
| 5,605,144 | A | 2/1997 | Simmons et al. |
| 5,609,620 | A | 3/1997 | Daily |
| 5,620,482 | A | 4/1997 | Augustine et al. |
| 5,624,477 | A | 4/1997 | Armond |
| 5,634,940 | A | 6/1997 | Panyard |
| 5,640,728 | A | 6/1997 | Graebe |
| 5,645,855 | A | 7/1997 | Lorenz |
| 5,658,325 | A | 8/1997 | Augustine |
| 5,662,695 | A | 9/1997 | Mason et al. |
| 5,683,439 | A | 11/1997 | Jensen |
| 5,720,774 | A | 2/1998 | Glucksman |
| 5,733,318 | A | 3/1998 | Augustine |
| 5,755,755 | A | 5/1998 | Panyard |
| 5,785,716 | A | 7/1998 | Bayron et al. |
| 5,806,335 | A | 9/1998 | Herbert et al. |
| 5,824,025 | A | 10/1998 | Augustine |
| 5,837,002 | A | 11/1998 | Augustine et al. |
| 5,840,080 | A | 11/1998 | Der Ovanesian |
| 5,843,145 | A | 12/1998 | Brink |
| 5,871,526 | A | 2/1999 | Gibbs et al. |
| 5,879,378 | A | 3/1999 | Usui |
| 5,887,437 | A | 3/1999 | Maxim |
| 5,913,849 | A | 6/1999 | Sundstrom et al. |
| 5,948,012 | A | 9/1999 | Mahaffey et al. |
| 5,968,000 | A | 10/1999 | Harrison et al. |
| 5,986,163 | A | 11/1999 | Augustine |
| 5,989,285 | A | 11/1999 | DeVilbiss et al. |
| 6,010,528 | A | 1/2000 | Augustine et al. |
| 6,019,783 | A | 2/2000 | Philips et al. |
| 6,030,412 | A | 2/2000 | Klatz et al. |
| 6,047,106 | A | 4/2000 | Salyer |
| 6,074,415 | A | 6/2000 | Der Ovanesian |
| 6,083,256 | A | 7/2000 | Der Ovanesian |
| 6,083,418 | A | 7/2000 | Czarnecki et al. |
| 6,117,164 | A | 9/2000 | Gildersleeve et al. |
| 6,176,869 | B1 | 1/2001 | Mason et al. |
| 6,176,870 | B1 | 1/2001 | Augustine |
| 6,185,744 | B1 | 2/2001 | Poholski |
| 6,188,930 | B1 | 2/2001 | Carson |
| 6,189,149 | B1 | 2/2001 | Allen |
| 6,189,550 | B1 | 2/2001 | Stickel et al. |
| 6,197,045 | B1 | 3/2001 | Carson |
| 6,234,538 | B1 | 5/2001 | Lauer |
| 6,238,427 | B1 | 5/2001 | Matta |
| 6,255,552 | B1 | 7/2001 | Cummings et al. |
| 6,257,011 | B1 | 7/2001 | Siman-Tov et al. |
| 6,290,716 | B1 | 9/2001 | Augustine |
| 6,336,935 | B1 | 1/2002 | Davis et al. |
| 6,349,560 | B1 | 2/2002 | Maier-Laxhuber et al. |
| 6,352,550 | B1 | 3/2002 | Gildersleeve et al. |
| 6,364,937 | B1 | 4/2002 | McMahon |
| 6,371,976 | B1 | 4/2002 | Vrzalik et al. |
| 6,375,674 | B1 | 4/2002 | Carson |
| 6,389,839 | B1 | 5/2002 | Sabin |
| 6,436,130 | B1 | 8/2002 | Philips et al. |
| 6,451,036 | B1 | 9/2002 | Heitzmann et al. |
| 6,454,792 | B1 | 9/2002 | Noda et al. |
| 6,461,379 | B1 | 10/2002 | Carson et al. |
| 6,463,212 | B1 | 10/2002 | Salyer |
| 6,503,297 | B1 | 1/2003 | Lu et al. |
| 6,508,831 | B1 | 1/2003 | Kushnir |
| 6,508,859 | B1 | 1/2003 | Zia et al. |
| 6,511,501 | B1 | 1/2003 | Augustine et al. |
| 6,511,502 | B2 | 1/2003 | Fletcher |
| 6,517,510 | B1 | 2/2003 | Stewart et al. |
| D471,987 | S | 3/2003 | Hoglund et al. |
| D472,322 | S | 3/2003 | Hoglund et al. |
| 6,551,348 | B1 | 4/2003 | Blalock et al. |
| D474,544 | S | 5/2003 | Hoglund et al. |
| 6,559,096 | B1 | 5/2003 | Smith et al. |
| 6,584,797 | B1 | 7/2003 | Smith et al. |
| 6,591,630 | B2 | 7/2003 | Smith et al. |
| 6,601,404 | B1 | 8/2003 | Roderick |
| 6,613,030 | B1 | 9/2003 | Coles et al. |
| 6,620,187 | B2 | 9/2003 | Carson et al. |
| 6,620,188 | B1 | 9/2003 | Ginsburg et al. |
| 6,645,232 | B2 | 11/2003 | Carson |
| 6,648,905 | B2 | 11/2003 | Hoglund et al. |
| 6,653,607 | B2 | 11/2003 | Ellis et al. |
| D483,125 | S | 12/2003 | Hoglund et al. |
| 6,660,027 | B2 | 12/2003 | Gruszecki et al. |

(56) References Cited

U.S. PATENT DOCUMENTS 6,669,715 B2 12/2003 Hoglund et al.
6,682,525 B2 1/2004 Lalonde et al.
D487,147 S 2/2004 Ellingboe et al.
D487,148 S 2/2004 Ellingboe et al.
6,688,132 B2 2/2004 Smith et al.
6,692,518 B2 2/2004 Carson
6,699,267 B2 3/2004 Voorhees et al.
6,701,724 B2 3/2004 Smith et al.
6,743,250 B2 6/2004 Renfro
6,755,801 B2 6/2004 Utterberg et al.
6,755,852 B2 6/2004 Lachenbruch et al.
D492,773 S 7/2004 Ellingboe et al.
6,770,848 B2 8/2004 Haas et al.
6,799,063 B2 9/2004 Carson
6,800,087 B2 10/2004 Papay et al.
6,802,855 B2 10/2004 Ellingboe et al.
6,802,885 B2 10/2004 Luk et al.
6,818,012 B2 11/2004 Ellingboe
6,827,728 B2 12/2004 Ellingboe et al.
6,846,322 B2 1/2005 Kane et al.
6,858,068 B2 2/2005 Smith et al.
6,878,156 B1 4/2005 Noda
6,893,453 B2 5/2005 Agarwal et al.
6,904,956 B2 6/2005 Noel
6,909,074 B1 6/2005 Bradley
6,921,198 B2 7/2005 Gruszecki et al.
6,931,875 B1 8/2005 Allen et al.
6,942,644 B2 9/2005 Worthen
6,960,243 B1 11/2005 Smith et al.
6,968,711 B2 11/2005 Smith et al.
6,969,399 B2 11/2005 Schock et al.
7,008,445 B2 3/2006 Lennox
7,022,099 B2 4/2006 Litzie et al.
7,044,960 B2 5/2006 Voorhees et al.
7,052,509 B2 5/2006 Lennox et al.
7,055,575 B2 6/2006 Noel
7,056,335 B2 6/2006 Agarwal et al.
7,063,718 B2 6/2006 Dobak, III
7,077,858 B2 7/2006 Fletcher et al.
7,097,657 B2 8/2006 Noda et al.
7,101,389 B1 9/2006 Augustine et al.
7,122,047 B2 10/2006 Grahn et al.
7,160,316 B2 1/2007 Hamilton et al.
7,172,586 B1 2/2007 Dae et al.
7,240,720 B2 7/2007 Noel
7,303,554 B2 12/2007 Lalonde et al.
7,303,579 B2 12/2007 Schock et al.
7,338,516 B2 3/2008 Quincy, III et al.
7,361,186 B2 4/2008 Voorhees et al.
7,377,935 B2 5/2008 Schock et al.
7,507,250 B2 3/2009 Lennox
7,517,360 B2 4/2009 Frey et al.
RE40,815 E 6/2009 Kudaravalli et al.
7,547,320 B2 6/2009 Schook et al.
RE40,868 E 8/2009 Ryba et al.
7,621,944 B2 11/2009 Wilson et al.
7,621,945 B2 11/2009 Lennox et al.
7,666,213 B2 2/2010 Freedman, Jr. et al.
7,678,716 B2 3/2010 Yahiaoui et al.
7,686,840 B2 3/2010 Quincy, III et al.
7,727,228 B2 6/2010 Abboud et al.
7,731,739 B2 6/2010 Schock et al.
7,744,640 B1 6/2010 Faries, Jr. et al.
7,749,261 B2 7/2010 Hansen et al.
7,763,061 B2 7/2010 Schorr et al.
7,771,461 B2 8/2010 Schock et al.
7,784,304 B2 8/2010 Trinh et al.
7,799,063 B2 9/2010 Ingram et al.
7,827,815 B2 11/2010 Carson et al.
7,867,266 B2 1/2011 Collins
7,892,269 B2 2/2011 Collins et al.
7,896,910 B2 3/2011 Schirrmacher et al.
7,918,243 B2 4/2011 Diodati et al.
8,047,010 B2 11/2011 Carson et al.
8,052,624 B2 11/2011 Buchanan et al.
8,066,752 B2 11/2011 Hamilton et al.
8,182,521 B2 5/2012 Kane et al.
8,187,697 B2 5/2012 Quincy, III et al.
8,216,163 B2 7/2012 Edelman
8,283,602 B2 10/2012 Augustine et al.
8,454,671 B2 6/2013 Lennox et al.
D685,916 S 7/2013 Hoglund
8,491,644 B1 7/2013 Carson et al.
8,597,217 B2 12/2013 Lowe et al.
8,597,339 B2 12/2013 Augustine et al.
8,603,150 B2 12/2013 Kane et al.
8,632,576 B2 1/2014 Quisenberry
8,647,374 B2 2/2014 Koewler
8,715,330 B2 5/2014 Lowe et al.
8,778,119 B2 7/2014 Starr et al.
8,808,344 B2 8/2014 Scott et al.
8,840,581 B2 9/2014 McGill et al.
9,034,458 B2 5/2015 Li
9,078,742 B2 7/2015 Quincy, III et al.
9,089,462 B1 7/2015 Lafleche
9,211,358 B2 12/2015 Sinko et al.
9,278,024 B2 3/2016 Scott et al.
9,333,112 B2 5/2016 Carson
9,552,706 B2 1/2017 Schneider, II et al.
9,566,185 B2 2/2017 Carson et al.
9,622,907 B2 4/2017 Carson et al.
9,687,386 B2 6/2017 Carson
9,763,823 B2 9/2017 Voorhees et al.
9,907,889 B2 3/2018 Locke et al.
10,010,452 B2 7/2018 Wenske et al.
10,123,902 B2 11/2018 Carson et al.
10,220,198 B2 3/2019 Fuchs et al.
10,258,501 B2 4/2019 Carson
10,376,412 B2 8/2019 Brienza et al.
10,441,458 B2 10/2019 Voorhees et al.
10,441,707 B2 10/2019 Voorhees et al.
10,548,778 B2 2/2020 Hassenpflug et al.
D887,426 S 6/2020 Matsushita
10,912,672 B1 2/2021 Jones et al.
D922,424 S 6/2021 Frueh et al.
D925,574 S 7/2021 Beko
D928,188 S 8/2021 Giannino et al.
11,173,071 B1 11/2021 Tawil et al.
D939,550 S 12/2021 Miyai et al.
11,234,859 B2 2/2022 Voorhees et al.
D947,216 S 3/2022 Leininger
11,285,039 B2 * 3/2022 Steele ...................... B64G 1/50
D948,534 S 4/2022 Bessette et al.
D952,666 S 5/2022 Sajan
D959,475 S 8/2022 Norman
D960,191 S 8/2022 Feit et al.
D973,067 S 12/2022 Oh et al.
11,975,123 B2 5/2024 Appel et al.
2001/0034545 A1 10/2001 Elkins
2001/0039439 A1 11/2001 Elkins et al.
2002/0007203 A1 1/2002 Gilmartin et al.
2002/0015689 A1 2/2002 Munro et al.
2002/0107558 A1 8/2002 Clifton et al.
2002/0111657 A1 8/2002 Dae et al.
2002/0138121 A1 9/2002 Fox
2002/0161419 A1 10/2002 Carson et al.
2003/0074038 A1 4/2003 Gruszecki et al.
2003/0078638 A1 4/2003 Voorhees et al.
2003/0078639 A1 4/2003 Carson
2003/0078640 A1 4/2003 Carson et al.
2003/0109911 A1 6/2003 Lachenbruch et al.
2003/0114903 A1 6/2003 Ellingboe
2003/0135252 A1 7/2003 MacHold et al.
2003/0149359 A1 8/2003 Smith
2003/0149461 A1 8/2003 Johnson
2003/0150232 A1 8/2003 Brudnicki
2003/0163179 A1 8/2003 Hoglund et al.
2003/0163180 A1 8/2003 Hoglund et al.
2003/0163183 A1 8/2003 Carson
2003/0163185 A1 8/2003 Carson
2003/0212416 A1 11/2003 Cinelli et al.
2004/0030372 A1 2/2004 Ellingboe et al.
2004/0030373 A1 2/2004 Ellingboe et al.
2004/0059212 A1 3/2004 Abreu

(56) References Cited

U.S. PATENT DOCUMENTS

2004/0064170 A1 4/2004 Radons et al.
2004/0073280 A1 4/2004 Dae et al.
2004/0082886 A1 4/2004 Timpson
2004/0087606 A1 5/2004 Voorhees et al.
2004/0133253 A1 7/2004 Grahn et al.
2004/0158303 A1 8/2004 Lennox et al.
2004/0225341 A1 11/2004 Schock et al.
2004/0243122 A1 12/2004 Auth et al.
2004/0252750 A1 12/2004 Gruszecki et al.
2004/0255362 A1* 12/2004 Soerens ............... A41D 31/102 2/161.7
2004/0260369 A1 12/2004 Schock et al.
2004/0267339 A1 12/2004 Yon et al.
2005/0028551 A1 2/2005 Noda et al.
2005/0060012 A1 3/2005 Voorhees et al.
2005/0065583 A1 3/2005 Voorhees et al.
2005/0096714 A1 5/2005 Freedman et al.
2005/0177212 A1 8/2005 Njemanze
2005/0187502 A1 8/2005 Krempel et al.
2005/0244629 A1 11/2005 Usui et al.
2005/0288749 A1 12/2005 Lachenbruch
2006/0024053 A1 2/2006 Grant
2006/0030916 A1 2/2006 Lennox
2006/0036304 A1 2/2006 Cordani et al.
2006/0058858 A1 3/2006 Smith
2006/0074469 A1 4/2006 Lennox et al.
2006/0122673 A1 6/2006 Callister et al.
2006/0124141 A1 6/2006 Dobak
2006/0136023 A1 6/2006 Dobak
2006/0161232 A1 7/2006 Kasza et al.
2006/0190066 A1 8/2006 Worthen
2006/0235114 A1 10/2006 Kitazono et al.
2006/0247744 A1 11/2006 Nest et al.
2006/0276089 A1 12/2006 Amarasinghe et al.
2006/0287697 A1 12/2006 Lennox
2006/0293734 A1 12/2006 Scott et al.
2007/0043409 A1 2/2007 Brian et al.
2007/0049997 A1 3/2007 Fields et al.
2007/0054122 A1 3/2007 Paisner et al.
2007/0068931 A1 3/2007 Augustine et al.
2007/0073368 A1 3/2007 Cazzini et al.
2007/0100404 A1 5/2007 Ko et al.
2007/0173735 A1 7/2007 Callister et al.
2007/0213793 A1 9/2007 Hayes
2007/0225782 A1 9/2007 Taylor
2007/0244475 A1 10/2007 Carson et al.
2007/0270925 A1 11/2007 Levinson
2008/0027523 A1 1/2008 Behringer et al.
2008/0046046 A1 2/2008 Ginsburg
2008/0114431 A1 5/2008 Ginsburg
2008/0147152 A1 6/2008 Quincy et al.
2008/0249524 A1 10/2008 Dunning
2008/0255644 A1 10/2008 Carson
2008/0275534 A1 11/2008 Noel
2009/0018504 A1 1/2009 Pile-Spellman et al.
2009/0043366 A1 2/2009 Dae
2009/0066079 A1 3/2009 Miros et al.
2009/0088825 A1 4/2009 Ota
2009/0099629 A1 4/2009 Carson et al.
2009/0131835 A1 5/2009 Voorhees et al.
2009/0149925 A1 6/2009 MacDonald et al.
2009/0157000 A1 6/2009 Waller
2009/0177184 A1 7/2009 Christensen et al.
2009/0182400 A1 7/2009 Dae et al.
2009/0228082 A1 9/2009 Ross, III et al.
2009/0250367 A1 10/2009 Murdoch et al.
2009/0280182 A1 11/2009 Beck et al.
2009/0287283 A1 11/2009 Biser et al.
2009/0299287 A1 12/2009 Carson et al.
2009/0312823 A1 12/2009 Patience et al.
2009/0326619 A1 12/2009 Kagan
2010/0016933 A1 1/2010 Chen et al.
2010/0168825 A1 7/2010 Barbknecht
2010/0198122 A1 8/2010 Freund
2010/0198320 A1 8/2010 Pierre et al.
2010/0204765 A1 8/2010 Hall et al.
2010/0241073 A1 9/2010 Andersen et al.
2010/0312202 A1 12/2010 Henley et al.
2011/0021960 A1 1/2011 Filtvedt et al.
2011/0029051 A1 2/2011 Ross
2011/0045056 A1 2/2011 Munro et al.
2011/0125238 A1 5/2011 Nofzinger
2011/0152982 A1 6/2011 Richardson
2011/0166633 A1 7/2011 Stull
2011/0172749 A1 7/2011 Christensen et al.
2011/0306972 A1 12/2011 Widenhouse et al.
2011/0307040 A1 12/2011 Peterson
2011/0308781 A1 12/2011 O'Riordan et al.
2011/0313497 A1 12/2011 Mcfarlane
2012/0046720 A1 2/2012 Ishizaki
2012/0065715 A1 3/2012 Carson
2012/0080031 A1 4/2012 Belson
2012/0095536 A1 4/2012 Machold et al.
2012/0172774 A1 7/2012 Lowe et al.
2012/0185021 A1 7/2012 Johnson et al.
2012/0191035 A1 7/2012 Stephan
2012/0204881 A1* 8/2012 Davidson .......... A61M 16/0605 128/206.25
2012/0220960 A1 8/2012 Ruland
2012/0288848 A1 11/2012 Latham et al.
2013/0023808 A1 1/2013 Brown et al.
2013/0116760 A1 5/2013 Carson et al.
2013/0138185 A1 5/2013 Paxman et al.
2013/0190667 A1* 7/2013 Kane ....................... A61F 7/007 601/149
2013/0238042 A1 9/2013 Gildersleeve et al.
2013/0310725 A1 11/2013 Jerrells et al.
2014/0039451 A1 2/2014 Bangera et al.
2014/0046411 A1 2/2014 Elkins et al.
2014/0172050 A1 6/2014 Dabrowiak
2014/0214138 A1* 7/2014 Voorhees .................. A61F 7/10 607/104
2014/0222121 A1 8/2014 Spence et al.
2014/0228717 A1 8/2014 Parish et al.
2014/0228918 A1 8/2014 Brienza et al.
2014/0276253 A1 9/2014 Varga et al.
2014/0277301 A1 9/2014 Varga et al.
2014/0288621 A1 9/2014 Efremkin
2014/0316494 A1 10/2014 Augustine et al.
2014/0343639 A1 11/2014 Hopper et al.
2015/0025606 A1 1/2015 Davis
2015/0051673 A1 2/2015 Rivas Tapia
2015/0173942 A1 6/2015 Whitely
2015/0209192 A1 7/2015 Manion et al.
2015/0223972 A1 8/2015 Dabrowiak
2015/0230973 A1 8/2015 Dabrowiak et al.
2015/0250643 A1 9/2015 Paradis
2015/0290042 A1 10/2015 Freer et al.
2015/0366703 A1 12/2015 Du
2015/0373781 A1 12/2015 Augustine et al.
2016/0008166 A1 1/2016 Voorhees et al.
2016/0022477 A1 1/2016 Schaefer et al.
2016/0038336 A1 2/2016 Hilton et al.
2016/0310316 A1 10/2016 Hixson, Jr.
2016/0324683 A1 11/2016 Carson
2017/0049618 A1 2/2017 Ward et al.
2017/0135855 A1 5/2017 Stefan et al.
2017/0151087 A1 6/2017 Carson et al.
2017/0189225 A1 7/2017 Voorhees et al.
2017/0224528 A1 8/2017 Berg et al.
2017/0246029 A1 8/2017 Clark
2017/0246031 A1 8/2017 Benyaminpour et al.
2017/0246374 A1 8/2017 Voorhees et al.
2017/0348144 A1 12/2017 Taylor et al.
2017/0348145 A1 12/2017 Voorhees et al.
2017/0354534 A1 12/2017 Paradis et al.
2018/0000255 A1 1/2018 Youngblood et al.
2018/0014967 A1 1/2018 Taylor
2018/0042762 A1 2/2018 Galer
2018/0042763 A1 2/2018 Galer et al.
2018/0064594 A1 3/2018 Finch, Jr. et al.
2018/0207024 A1 7/2018 Dabrowiak et al.
2018/0214297 A1 8/2018 Hughett et al.
2018/0214302 A1 8/2018 Dabrowiak et al.

(56) References Cited

U.S. PATENT DOCUMENTS

| | | | |
|---|---|---|---|
| 2018/0263677 | A1 | 9/2018 | Hilton et al. |
| 2018/0376539 | A1 | 12/2018 | Augustine et al. |
| 2019/0083322 | A1 | 3/2019 | Huang et al. |
| 2019/0085644 | A1 | 3/2019 | Ames et al. |
| 2019/0099288 | A1 | 4/2019 | Vergara et al. |
| 2019/0117446 | A1 | 4/2019 | Carson et al. |
| 2019/0192337 | A1 | 6/2019 | Taylor et al. |
| 2019/0201574 | A1 | 7/2019 | Delury et al. |
| 2019/0262169 | A1 | 8/2019 | Vergara et al. |
| 2019/0331277 | A1 | 10/2019 | Vachon |
| 2020/0001022 | A1 | 1/2020 | Landy, III et al. |
| 2020/0071051 | A1 | 3/2020 | Lewis |
| 2020/0155341 | A1 | 5/2020 | Voorhees et al. |
| 2020/0246180 | A1 | 8/2020 | Liang et al. |
| 2020/0345971 | A1 | 11/2020 | Schirm et al. |
| 2020/0405530 | A1 | 12/2020 | Taylor et al. |
| 2021/0060230 | A1 | 3/2021 | Hopper et al. |
| 2022/0087874 | A1 | 3/2022 | Schneider et al. |
| 2022/0151821 | A1 | 5/2022 | Voorhees et al. |
| 2022/0192865 | A1 | 6/2022 | Hughett, Sr. et al. |
| 2022/0192867 | A1 | 6/2022 | Stich et al. |
| 2022/0233344 | A1 | 7/2022 | Hoglund |
| 2022/0265468 | A1 | 8/2022 | Xu et al. |
| 2022/0280336 | A1 | 9/2022 | Smith et al. |
| 2022/0287875 | A1 | 9/2022 | Minchew et al. |
| 2022/0287876 | A1 | 9/2022 | Smith et al. |
| 2022/0296413 | A1 | 9/2022 | Jones |
| 2022/0296414 | A1 | 9/2022 | Bible et al. |
| 2022/0304847 | A1 | 9/2022 | Kuroda et al. |
| 2022/0313478 | A1 | 10/2022 | Johnston |
| 2022/0347009 | A1 | 11/2022 | Hughett, Sr. et al. |
| 2022/0401259 | A1 | 12/2022 | Basciano et al. |
| 2022/0406017 | A1 | 12/2022 | Wang et al. |
| 2023/0000668 | A1 | 1/2023 | Walker et al. |
| 2023/0009524 | A1 | 1/2023 | Johnston et al. |
| 2023/0011631 | A1 | 1/2023 | Yin et al. |
| 2023/0019048 | A1 | 1/2023 | Stich et al. |
| 2023/0021245 | A1 | 1/2023 | Walker et al. |
| 2023/0040583 | A1 | 2/2023 | Falis et al. |
| 2023/0077318 | A9 | 3/2023 | Voorhees et al. |
| 2023/0190519 | A1 | 6/2023 | Stich et al. |
| 2024/0065884 | A1 | 2/2024 | Fallows et al. |
| 2024/0082052 | A1 | 3/2024 | Cho et al. |
| 2024/0091054 | A1 | 3/2024 | Boone-Worthman et al. |
| 2024/0099878 | A1 | 3/2024 | Voorhees et al. |
| 2024/0108497 | A1 | 4/2024 | Daw et al. |
| 2024/0366422 | A1 | 11/2024 | Johnston et al. |
| 2025/0032310 | A1 | 1/2025 | Stich et al. |
| 2025/0041107 | A1 | 2/2025 | Walker et al. |
| 2025/0110628 | A1 | 4/2025 | Litman et al. |
| 2025/0134705 | A1 | 5/2025 | Stich et al. |
| 2025/0143918 | A1 | 5/2025 | Voorhees et al. |
| 2025/0161107 | A1 | 5/2025 | Stich et al. |
| 2025/0198550 | A1 | 6/2025 | Johnston et al. |

FOREIGN PATENT DOCUMENTS

| | | | | |
|---|---|---|---|---|
| CA | 2729122 | A1 | 7/2002 | |
| CN | 102026596 | A | 4/2011 | |
| CN | 101389372 | B | 8/2012 | |
| CN | 102746518 | A | 10/2012 | |
| CN | 103939695 | B | 3/2016 | |
| CN | 305928532 | | 7/2020 | |
| CN | 111643265 | A | 9/2020 | |
| CN | 306402573 | | 3/2021 | |
| CN | 113230017 | A | 8/2021 | |
| CN | 307690236 | | 11/2022 | |
| CN | 309180016 | | 3/2025 | |
| DE | 102014118510 | A1 | 6/2016 | |
| EP | 0862901 | A1 | 9/1998 | |
| EP | 1073388 | A1 | 2/2001 | |
| EP | 1616543 | A2 | 1/2006 | |
| EP | 1641503 | A2 | 4/2006 | |
| EP | 1718894 | B1 | 7/2010 | |
| EP | 2204150 | A1 | 7/2010 | |
| EP | 2269546 | A1 | 1/2011 | |
| GB | 2118440 | A | 11/1983 | |
| JP | H09508045 | A | 8/1997 | |
| JP | 2002-534160 | A | 10/2002 | |
| JP | 2007029638 | A | 2/2007 | |
| JP | 2013248293 | A | 12/2013 | |
| KR | 20110020420 | A * | 3/2011 | ........... A61F 7/0241 |
| WO | 9807397 | A1 | 2/1998 | |
| WO | 98/31310 | A1 | 7/1998 | |
| WO | 199944552 | A1 | 9/1999 | |
| WO | 9953874 | A1 | 10/1999 | |
| WO | 2000040185 | A1 | 7/2000 | |
| WO | 2003086253 | A2 | 10/2003 | |
| WO | 2004075949 | A2 | 9/2004 | |
| WO | 2005028984 | A1 | 3/2005 | |
| WO | 2005117546 | A2 | 12/2005 | |
| WO | 2007120677 | A2 | 10/2007 | |
| WO | 2009/090403 | A1 | 7/2009 | |
| WO | 2009147413 | A1 | 12/2009 | |
| WO | 2009148636 | A1 | 12/2009 | |
| WO | 2012125916 | A2 | 9/2012 | |
| WO | 2012138980 | A2 | 10/2012 | |
| WO | 2015084925 | A1 | 6/2015 | |
| WO | 2016057119 | A1 | 4/2016 | |
| WO | 2016123500 | A1 | 8/2016 | |
| WO | 2017/127768 | A1 | 7/2017 | |
| WO | 2018075576 | A1 | 4/2018 | |
| WO | 2022/159879 | A1 | 7/2022 | |
| WO | 2022155130 | A1 | 7/2022 | |
| WO | 2022155132 | A1 | 7/2022 | |
| WO | 2022159513 | A1 | 7/2022 | |
| WO | 2022/165068 | A1 | 8/2022 | |
| WO | 2022235513 | A1 | 11/2022 | |
| WO | 2023121674 | A1 | 6/2023 | |
| WO | 2023140870 | A1 | 7/2023 | |
| WO | 2023154050 | A1 | 8/2023 | |
| WO | 2023229609 | A1 | 11/2023 | |

OTHER PUBLICATIONS

PCT/US2016/015688 filed Jan. 29, 2016 International Search Report and Written Opinion dated Apr. 1, 2016.

PCT/US2022/013672 filed Jan. 25, 2022, International Search Report and Written Opinion dated Jul. 15, 2022.

PCT/US2022/014147 filed Jan. 27, 2022 International Search Report and Written Opinion dated Jul. 18, 2022.

U.S. Appl. No. 17/547,128, filed Dec. 9, 2021 Restriction Requirement dated Sep. 5, 2024.

U.S. Appl. No. 17/552,309, filed Dec. 15, 2021 Restriction Requirement dated Dec. 12, 2024.

U.S. Appl. No. 17/584,101, filed Jan. 25, 2022 Restriction Requirement dated Nov. 5, 2024.

U.S. Appl. No. 17/689,791, filed Mar. 8, 2022 Non-Final Office Action dated Dec. 30, 2024.

U.S. Appl. No. 17/689,791, filed Mar. 8, 2022 Restriction Requirement dated Oct. 16, 2024.

U.S. Appl. No. 17/690,908, filed Mar. 9, 2022 Non-Final Office Action dated Dec. 18, 2024.

U.S. Appl. No. 17/691,990, filed Mar. 10, 2022 Non-Final Office Action dated Dec. 17, 2024.

U.S. Appl. No. 17/691,990, filed Mar. 10, 2022 Restriction Requirement dated Oct. 16, 2024.

U.S. Appl. No. 17/694,416, filed Mar. 14, 2022 Restriction Requirement dated Nov. 8, 2024.

U.S. Appl. No. 17/709,019, filed Mar. 30, 2022 Non-Final Office Action dated Dec. 31, 2024.

U.S. Appl. No. 17/709,019, filed Mar. 30, 2022 Restriction Requirement dated Oct. 16, 2024.

U.S. Appl. No. 17/723,210, filed Apr. 18, 2022 Non-Final Office Action dated Dec. 20, 2024.

U.S. Appl. No. 17/723,210, filed Apr. 18, 2022 Restriction Requirement dated Oct. 16, 2024.

U.S. Appl. No. 17/848,074, filed Jun. 23, 2022 Notice of Allowance dated Nov. 26, 2024.

(56) References Cited

OTHER PUBLICATIONS

U.S. Appl. No. 17/849,419, filed Jun. 24, 2022 Non-Final Office Action dated Nov. 8, 2024.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCTUS2022011971 filed Jan. 11, 2022 International Search Report and Written Opinion dated Apr. 21, 2022.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
U.S. Appl. No. 17/589,849, filed Jan. 31, 2022 Notice of Allowance dated Aug. 23, 2023.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thrcn.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
PCT/US2015/045548 filed Aug. 17, 2015 International Search Report and Written Opinion dated Nov. 24, 2015.
Sevgi, M., et. al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
PCT/US2021/065144 filed Dec. 23, 2021 International Search Report dated Oct. 4, 2022.
PCT/US2022/026999 filed Apr. 29, 2022 International Search Report and Written Opinion dated Oct. 24, 2022.
U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 17/848,074, filed Jun. 23, 2022 Non-Final Office Action dated Nov. 30, 2023.
U.S. Appl. No. 18/536,087, filed Dec. 11, 2023 Non-Final Office Action dated Jun. 28, 2024.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/686,301, filed Mar. 3, 2022 Non-Final Office Action dated Oct. 1, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Notice of Allowance dated Aug. 29, 2024.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/584,101, filed Jan. 25, 2022 Non-Final Office Action dated Feb. 5, 2025.
U.S. Appl. No. 17/678,965, filed Feb. 23, 2022 Non-Final Office Action dated Feb. 12, 2025.
U.S. Appl. No. 17/686,301, filed Mar. 3, 2022 Advisory Action dated Apr. 4, 2025.
U.S. Appl. No. 17/686,301, filed Mar. 3, 2022 Final Office Action dated Jan. 29, 2025.
U.S. Appl. No. 17/694,416, filed Mar. 14, 2022 Non-Final Office Action dated Jan. 22, 2025.
U.S. Appl. No. 17/700,216, filed Mar. 21, 2022 Non-Final Office Action dated Feb. 5, 2025.
U.S. Appl. No. 17/849,419, filed Jun. 24, 2022 Final Office Action dated Feb. 14, 2025.
U.S. Appl. No. 17/857,997, filed Jul. 5, 2022 Non-Final Office Action dated Apr. 28, 2025.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Non-Final Office Action dated Apr. 28, 2025.
U.S. Appl. No. 17/881,270, filed Aug. 4, 2022 Restriction Requirement dated Feb. 11, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
U.S. Appl. No. 17/552,309, filed Dec. 15, 2021 Final Office Action dated Jul. 30, 2025.
U.S. Appl. No. 17/678,965, filed Feb. 23, 2022 Notice of Allowance dated Jun. 3, 2025.
U.S. Appl. No. 17/686,301, filed Mar. 3, 2022 Non-Final Office Action dated May 14, 2025.
U.S. Appl. No. 17/689,791, filed Mar. 8, 2022 Advisory Action dated Jul. 24, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/691,990, filed Mar. 10, 2022 Advisory Action dated Jul. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Advisory Action dated Jul. 24, 2025.
U.S. Appl. No. 17/709,019, filed Mar. 30, 2022 Final Office Action dated Jun. 15, 2025.
U.S. Appl. No. 17/723,210, filed Apr. 18, 2022 Advisory Action dated Jul. 31, 2025.
U.S. Appl. No. 17/723,210, filed Apr. 18, 2022 Final Office Action dated May 21, 2025.
U.S. Appl. No. 17/848,039, filed Jun. 23, 2021 Non-Final Office Action dated Jul. 29, 2025.
U.S. Appl. No. 17/849,419, filed Jun. 24, 2022 Non-Final Office Action dated Jun. 13, 2025.
U.S. Appl. No. 18/085,566, filed Dec. 20, 2022 Restriction Requirement dated May 16, 2025.

(56) References Cited

OTHER PUBLICATIONS

U.S. Appl. No. 18/272,026, filed Jul. 12, 2023 Non-Final Office Action dated Jul. 31, 2025.

* cited by examiner

FIG. 4C
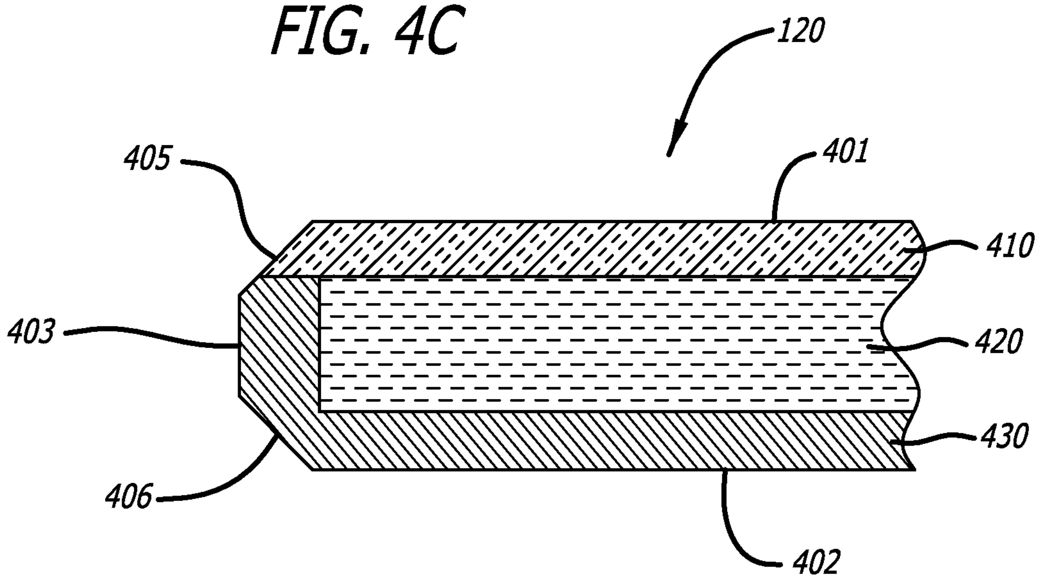
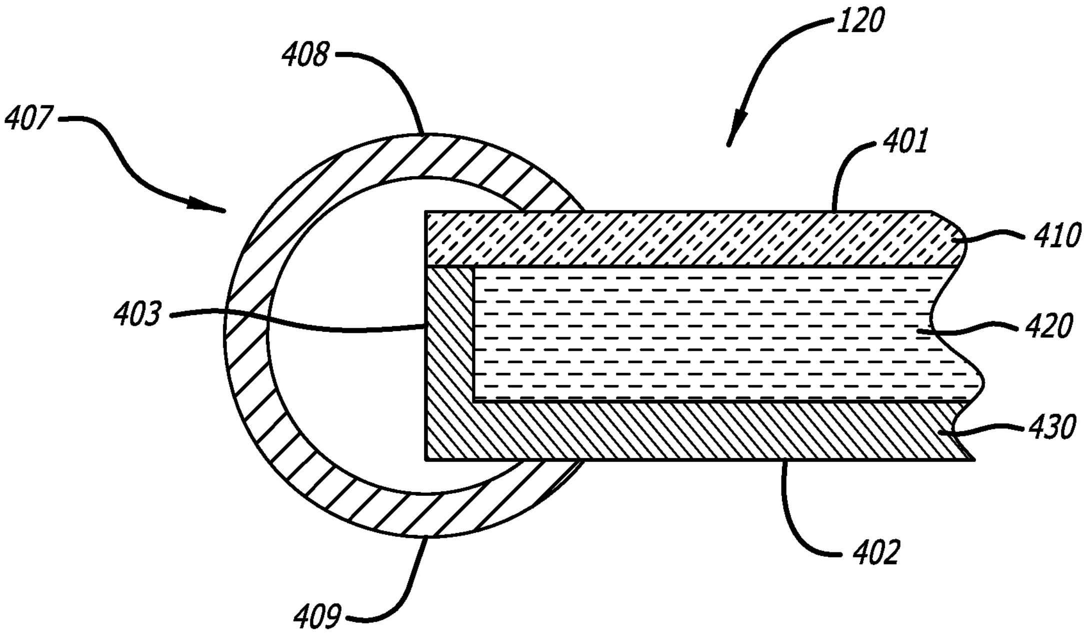
FIG. 4D

TRANSPARENT PAD

PRIORITY

This application claims the benefit of priority to U.S. Provisional Application No. 63/141,358, filed Jan. 25, 2021, which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled to a patient to affect surface-to-surface thermal energy exchange with the patient. In general, TTM systems include a TTM fluid control module coupled to at least one contact pad via a fluid deliver line. One such TTM system is disclosed in U.S. Pat. No. 6,645,232, titled "Patient Temperature Control System with Fluid Pressure Maintenance" filed Oct. 11, 2001 and one such thermal contact pad and related system is disclosed in U.S. Pat. No. 6,197,045 titled "Cooling/heating Pad and System" filed Jan. 4, 1999, both of which are incorporated herein by reference in their entireties. As noted in the '045 patent, the ability to establish and maintain thermally intimate pad-to-patient contact is of importance to fully realizing medical efficacies with TTM systems.

In some instances, the application of a medical device such as a pad, for example, may cause some irritation of the patient's skin. In some instances, irritation may be caused by abrasion of the skin by the pad, particularly along a perimeter of the pad. In other instances, irritation of the skin may be caused by reduced breathability of the skin. In some instances, it may be advantageous for the clinician to visually observe the skin beneath the pad to assess the state of irritation so that corrective action may be taken to resolve the irritation. In a case of TTM therapy, it may be advantageous for the clinician to assess the state irrational without disrupting the TTM therapy. In summary, TTM systems and methods that minimize skin irritation and/or provide for easy assessment of skin irritation may reduce complications of performing the TTM therapy and reduce discomfort of the patient during TTM therapy. Disclosed herein are embodiments of devices and methods for resolving skin irritation while performing TTM therapy.

SUMMARY OF THE INVENTION

Briefly summarized, disclosed herein is a medical pad for exchanging thermal energy between a targeted temperature management (TTM) fluid and a patient. The pad includes a top side and a bottom side. The pad further includes a fluid containing layer disposed between the top side and the bottom side, wherein the fluid containing layer is configured for containing the TTM fluid. The fluid containing layer includes a fluid inlet and a fluid outlet and the TTM fluid is circulatable within the fluid containing layer from the fluid inlet to the fluid outlet. The pad further includes an insulation layer disposed the top side, and a thermal conduction layer disposed on the bottom side. In use, the pad is disposed in contact with a skin of a patient, and a perimeter of the pad is configured to inhibit irritation of the skin of the patient along the perimeter.

The pad may further include a chamfered edge extending along the perimeter of the pad, and in some embodiments, chamfered edge is a top edge of the pad. The pad may also include a rounded edge extending along the perimeter of the pad. The rounded edge may include a tube extending along the perimeter, a wall of the tube extends from the top side to the bottom side of the pad.

In some embodiments, the thermal conduction layer includes a skin contact surface configured to provide for breathability of the skin and the skin contact surface may be textured.

In some embodiments, the pad is configured to provide for visibility of the skin through the pad. At least a portion of the pad may be translucent. Each of the fluid containing layer and the thermal conduction layer may include a translucent portion, and the translucent portions may be coincident with each other. Each of the translucent portions may also be transparent.

The insulation layer may include at least one of an opening or translucent portion which may be disposed coincident with the translucent portions of the fluid containing layer and the thermal conduction layer.

The translucent portion of the insulation layer may include one or more air pockets, and in some embodiments, the translucent portion of the insulation layer is transparent.

In some embodiments, the pad includes a filter coupled to the fluid containing layer so that TTM fluid circulating through the fluid containing layer passes through the filter and the filter may include a porous wall disposed parallel to a continuous flow path through the filter.

Also disclosed herein is a method of providing a targeted temperature management (TTM) therapy to a patient. The method includes providing a TTM system including a TTM module configured to provide a TTM fluid, a thermal pad configured to receive the TTM fluid from the TTM module to facilitate thermal energy transfer between the TTM fluid and a patient, and a fluid delivery line (FDL) extending between the TTM module and the thermal pad, the FDL configured to provide TTM fluid flow between the TTM module and the thermal pad.

The thermal pad includes a top side, bottom side, and a fluid containing layer disposed between the top side and the bottom side. The fluid containing layer is configured for containing the TTM fluid and includes a fluid inlet and a fluid outlet, where the TTM fluid is circulatable within the fluid containing layer from the fluid inlet to the fluid outlet.

The thermal pad further includes an insulation layer disposed the top side and a thermal conduction layer disposed on the bottom side.

The method further includes applying the thermal pad to the patient, delivering the TTM fluid from the TTM module to the thermal pad, and visually observing the skin through a translucent portion of the thermal pad. The method may further include passing TTM fluid through a filter coupled to the fluid containing layer. In some embodiments, the thermal pad further includes a chamfered edge extending along a perimeter of the thermal pad. In other embodiments, the thermal pad further includes a rounded edge extending along a perimeter of the thermal pad. The thermal conduction layer may include a textured bottom surface to facilitate breathability of the skin beneath the thermal pad. In some embodiments, at least a portion of the thermal pad is translucent and the method further includes visually observing the skin through the translucent portion.

Also disclosed herein is a medical pad for exchanging thermal energy between a targeted temperature management (TTM) fluid and a patient. The pad includes a top side and a bottom side. The pad further includes a fluid containing layer disposed between the top side and the bottom side, wherein the fluid containing layer is configured for containing the TTM fluid. The fluid containing layer includes a fluid inlet and a fluid outlet and the TTM fluid is circulatable within the fluid containing layer from the fluid inlet to the fluid outlet. The pad further includes an insulation layer disposed the top side, and a thermal conduction layer disposed on the bottom side. In use, the pad is disposed in contact with a skin of a patient, and the pad is configured to provide for visibility of the skin through the pad.

At least a portion of the pad may be translucent. Each of the fluid containing layer and the thermal conduction layer may include a translucent portion, and the translucent portions may be coincident with each other. Each of the translucent portions may also be transparent.

The insulation layer may include at least one of an opening or translucent portion which may be disposed coincident with the translucent portions of the fluid containing layer and the thermal conduction layer.

The translucent portion of the insulation layer may include one or more air pockets, and in some embodiments, the translucent portion of the insulation layer is transparent.

The pad may further include a chamfered edge extending along the perimeter of the pad, and in some embodiments, chamfered edge is a top edge of the pad. The pad may also include a rounded edge extending along the perimeter of the pad. The rounded edge may include a tube extending along the perimeter, a wall of the tube extends from the top side to the bottom side of the pad.

In some embodiments, the thermal conduction layer includes a skin contact surface configured to provide for breathability of the skin and the skin contact surface may be textured.

In some embodiments, the pad includes a filter coupled to the fluid containing layer so that TTM fluid circulating through the fluid containing layer passes through the filter and the filter may include a porous wall disposed parallel to a continuous flow path through the filter.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4C is a detail cross-sectional side view of a portion of the thermal contact pad of FIG. 4A cut along sectioning lines 4C-4C illustrating an optional chamfered edge, in accordance with some embodiments.

FIG. 4D is a detail cross-sectional side view of a portion of the thermal contact pad of FIG. 4A cut along sectioning lines 4C-4C illustrating an optional rounded edge, in accordance with some embodiments.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of “a,” “an,” and “the” include plural references unless the context clearly dictates otherwise. The words “including,” “has,” and “having,” as used herein, including the claims, shall have the same meaning as the word “comprising.” Furthermore, the terms “or” and “and/or” as used herein are to be interpreted as inclusive or meaning any one or any combination. As an example, “A, B or C” or “A, B and/or C” mean “any of the following: A; B; C; A and B; A and C; B and C; A, B and C.” An exception to this definition will occur only when a combination of elements, components, functions, steps or acts are in some way inherently mutually exclusive.

The phrases “connected to” and “coupled to” refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Unless defined otherwise, all technical and scientific terms used herein have the same meaning as commonly understood by those of ordinary skill in the art.

Figure 1:
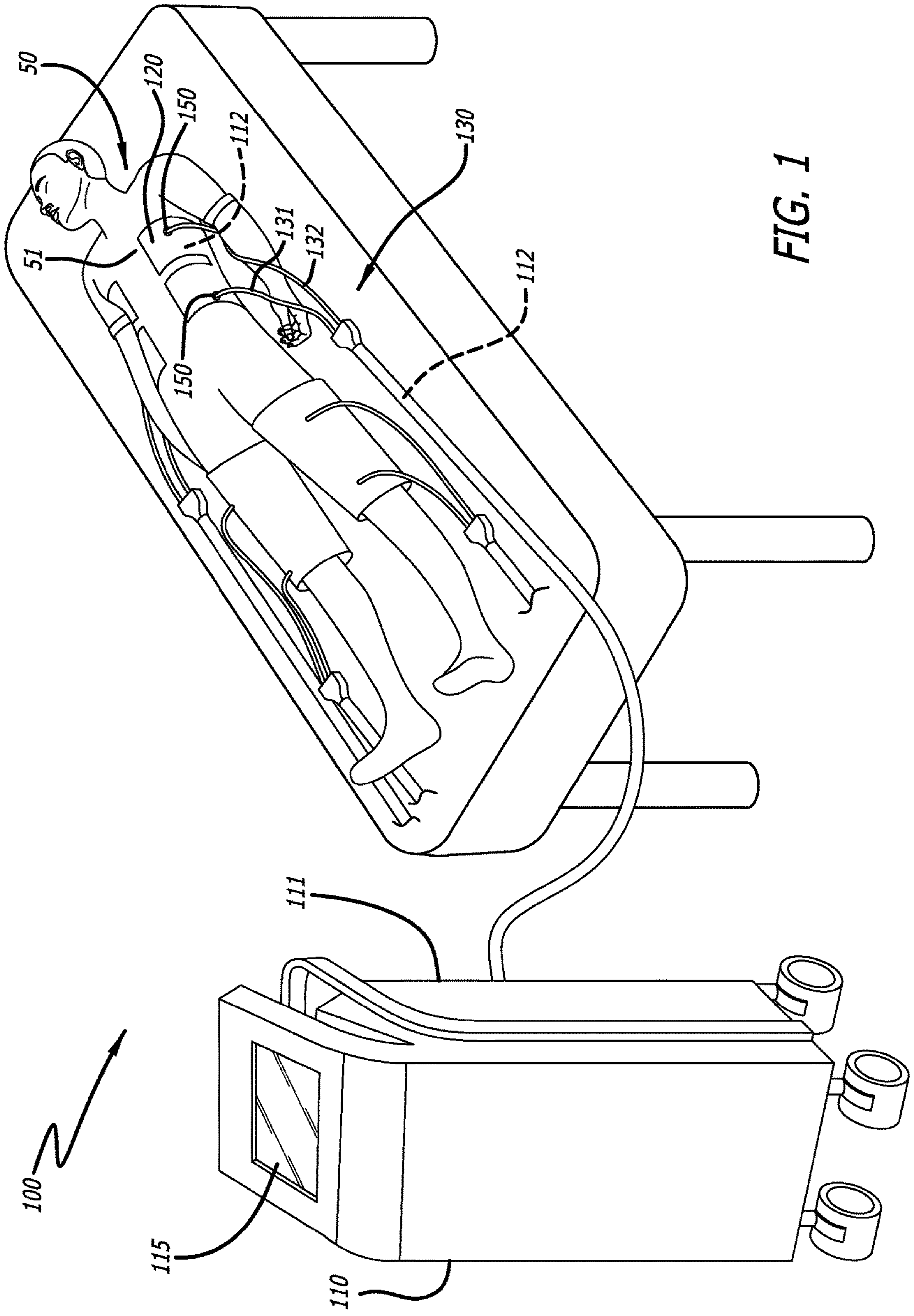
FIG. 1 illustrates a targeted temperature management (TTM) system for cooling or warming a patient, in accordance with some embodiments.

FIG. 1 illustrates a targeted temperature management (TTM) system 100 connected to a patient 50 for administering targeted temperature management therapy to the patient 50 which may include a cooling and/or warming of the patient 50, in accordance with some embodiments. The TTM system 100 includes a TTM module 110 including a graphical user interface (GUI) 115 enclosed within a module housing 111. The TTM system 100 includes a fluid deliver line (FDL) 130 extending from the TTM module 110 to a thermal contact pad 120 to provide for flow of TTM fluid 112 between the TTM module 110 and the pad 120. The FDL includes two conduits to facilitate delivery flow of TTM fluid 112 from the TTM module 110 to the pad 120 and return flow TTM fluid 112 from the pad 120 to the TTM module 110. In some embodiments, the two conduits may be attached to each other along a portion of a length of the FDL.

The TTM system 100 may include 1, 2, 3, 4 or more pads 120 and the TTM system 100 may include 1, 2, 3, 4 or more fluid delivery lines 130. In use, the TTM module 110 prepares the TTM fluid 112 for delivery to the pad 120 by heating or cooling the TTM fluid 112 to a defined temperature in accordance with a prescribed TTM therapy. The TTM module 110 circulates the TTM fluid 112 along a TTM fluid flow path including within the pad 120. The pad 120 is applied to the skin 51 of the patient to facilitate thermal energy exchange between the pad 120 and the patient 50. During the TTM therapy, the TTM module 110 may continually control the temperature of the TTM fluid 112 toward a target TTM temperature.

The FDL 130 includes at least a fluid delivery conduit 131 and a fluid return conduit 132. In use, the TTM fluid 112 may flow from the TTM module 110 through the fluid delivery conduit 131 to the pad 120. The TTM fluid 112 may then flow from thermal pad 120 through the fluid return conduit 132 to the TTM module 110. In some embodiments, the fluid delivery conduit 131 and the fluid return conduit 132 may be attached together along a portion of a length of the FDL 130. The fluid delivery conduit 131 and the fluid return conduit 132 may be separated from each other at each end of the FDL 130.

The TTM system 100 may include a connector system 150 to couple the FDL 130 to the pad 120. In some embodiments, the connector system 150 may couple a single fluid conduit of the FDL to the pad 120. Hence, the connection between the FDL 130 and the pad 120 may include more than one connector system 150 to couple more than one fluid conduit to the pad 120. The connector system 150 is further described below in FIGS. 4A and 4B.

Figure 2:
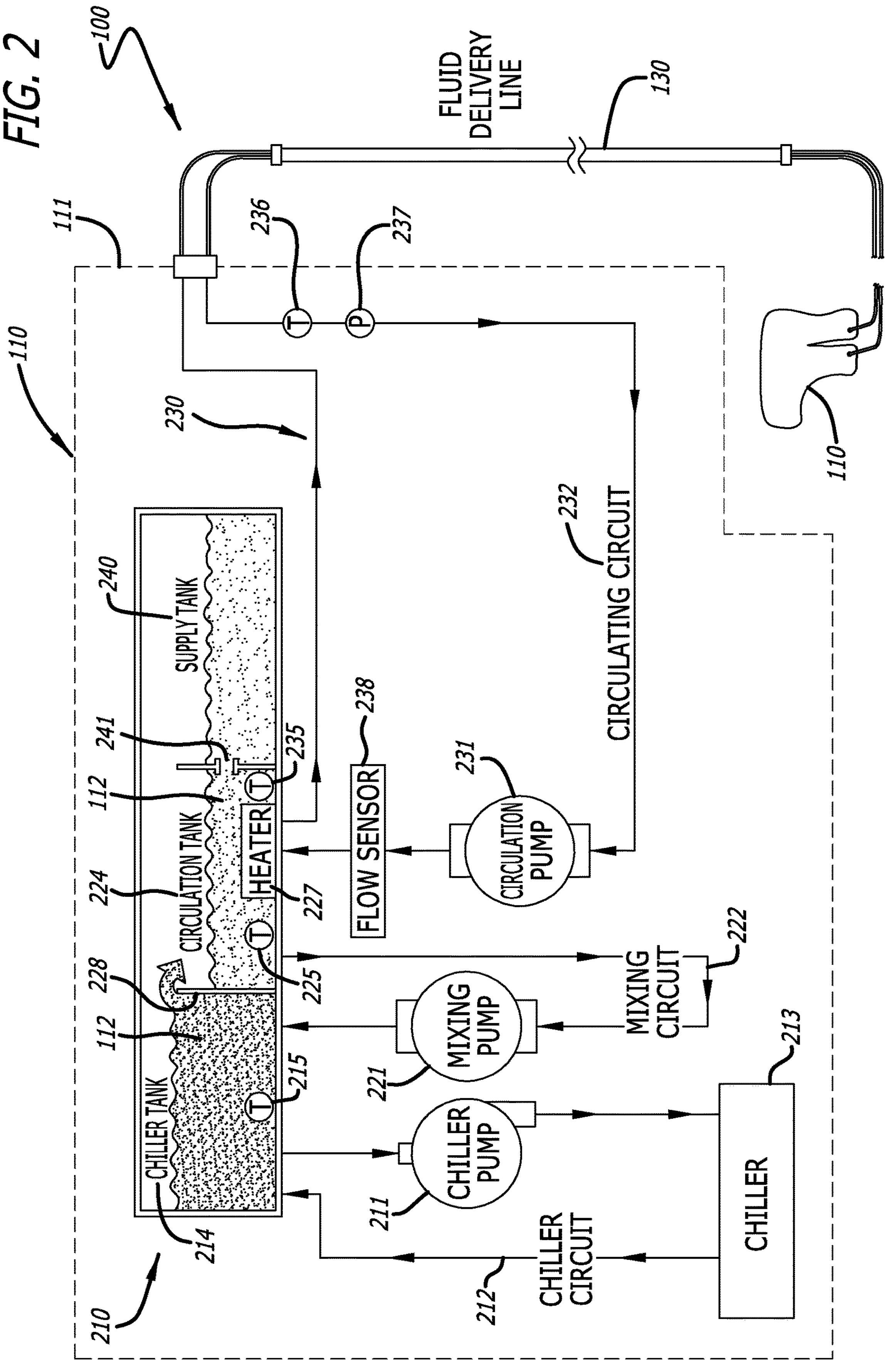
FIG. 2 illustrates a hydraulic schematic of the TTM system of FIG. 1, in accordance with some embodiments.

FIG. 2 illustrates a hydraulic schematic of the TTM system 100. The FDL 130 and the pad 120 are disposed external to the housing 111 of the TTM module 110. The TTM module includes various fluid sensors and fluid control devices to prepare and circulate the TTM fluid 112. The fluid subsystems of the TTM module may include a temperature control subsystem 210 and a circulation subsystem 230.

The temperature control subsystem 210 may include a chiller pump 211 to pump (recirculate) TTM fluid 112 through a chiller circuit 212 that includes a chiller 213 and a chiller tank 214. A temperature sensor 215 within the chiller tank 214 is configured to measure a temperature of the TTM fluid 112 within the chiller tank 214. The chiller 213 may be controlled by a temperature control logic (see FIG. 3) as further described below to establish a desired temperature of the TTM fluid 112 within chiller tank 214. In some instances, the temperature of the TTM fluid 112 within the chiller tank 214 may be less than the target temperature for the TTM therapy.

The temperature control subsystem 210 may further include a mixing pump 221 to pump TTM fluid 112 through a mixing circuit 222 that includes the chiller tank 214, a circulation tank 224, and a dam 228 disposed between the chiller tank 214 and circulation tank 224. The TTM fluid 112, when pumped by the mixing pump 221, enters the chiller tank 214 and mixes with the TTM fluid 112 within the chiller tank 214. The mixed TTM fluid 112 within the chiller tank 214 flows over the dam 228 and into the circulation tank 224. In other words, the mixing circuit 222 mixes the TTM fluid 112 within chiller tank 214 with the TTM fluid 112 within circulation tank 224 to cool the TTM fluid 112 within the circulation tank 224. A temperature sensor 225 within the circulation tank 224 measures the temperature of the TTM fluid 112 within the circulation tank 224. The temperature control logic may control the mixing pump 221 in accordance with temperature data from the temperature sensor 225 within the circulation tank 224.

The circulation tank 224 includes a heater 227 to increase to the temperature of the TTM fluid 112 within the circulation tank 224, and the heater 227 may be controlled by the temperature control logic. In summary, the temperature control logic when executed by the processor (see FIG. 3) may 1) receive temperature data from the temperature sensor 215 within the chiller tank and the temperature sensor 225 within the circulation tank 224 and 2) control the operation of the chiller 213, the chiller pump 211, the heater 227, and mixing pump 222 to establish and maintain the temperature of the TTM fluid 112 within the circulation tank 224 at the target temperature for the TTM therapy.

The circulation subsystem 230 includes a circulation pump 213 to pull TTM fluid 112 from the circulation tank 224 and through a circulating circuit 232 that includes the fluid delivery line 130 and the pad 120 located upstream of the circulation pump 213. The circulating circuit 232 also includes a pressure sensor 237 to represent a pressure of the TTM fluid 112 within the pad 120. The circulating circuit 232 includes a temperature sensor 235 within the circulation tank 224 to represent the temperature of the TTM fluid 112 entering the pad 120 and a temperature sensor 236 to represent the temperature of the TTM fluid exiting the pad 120. A flow meter 238 is disposed downstream of the circulation pump 213 to measure the flow rate of TTM fluid 112 through the circulating circuit 232 before the TTM fluid 112 re-enters that the circulation tank 224.

In use, the circulation tank 224, which may be vented to atmosphere, is located below (i.e., at a lower elevation than) the pad 120 so that a pressure within the pad 120 is less than atmospheric pressure (i.e., negative) when TTM fluid flow through the circulating circuit 232 is stopped. The pad 120 is also placed upstream of the circulation pump 231 to further establish a negative pressure within the pad 120 when the circulation pump 213 is operating. The fluid flow control logic (see FIG. 3) may control the operation of the circulation pump 213 to establish and maintain a desired negative pressure within the pad 120. A supply tank 240 provides TTM fluid 112 to the circulation tank 224 via a port 241 to maintain a defined volume of TTM fluid 112 within the circulation tank 224.

Figure 3:
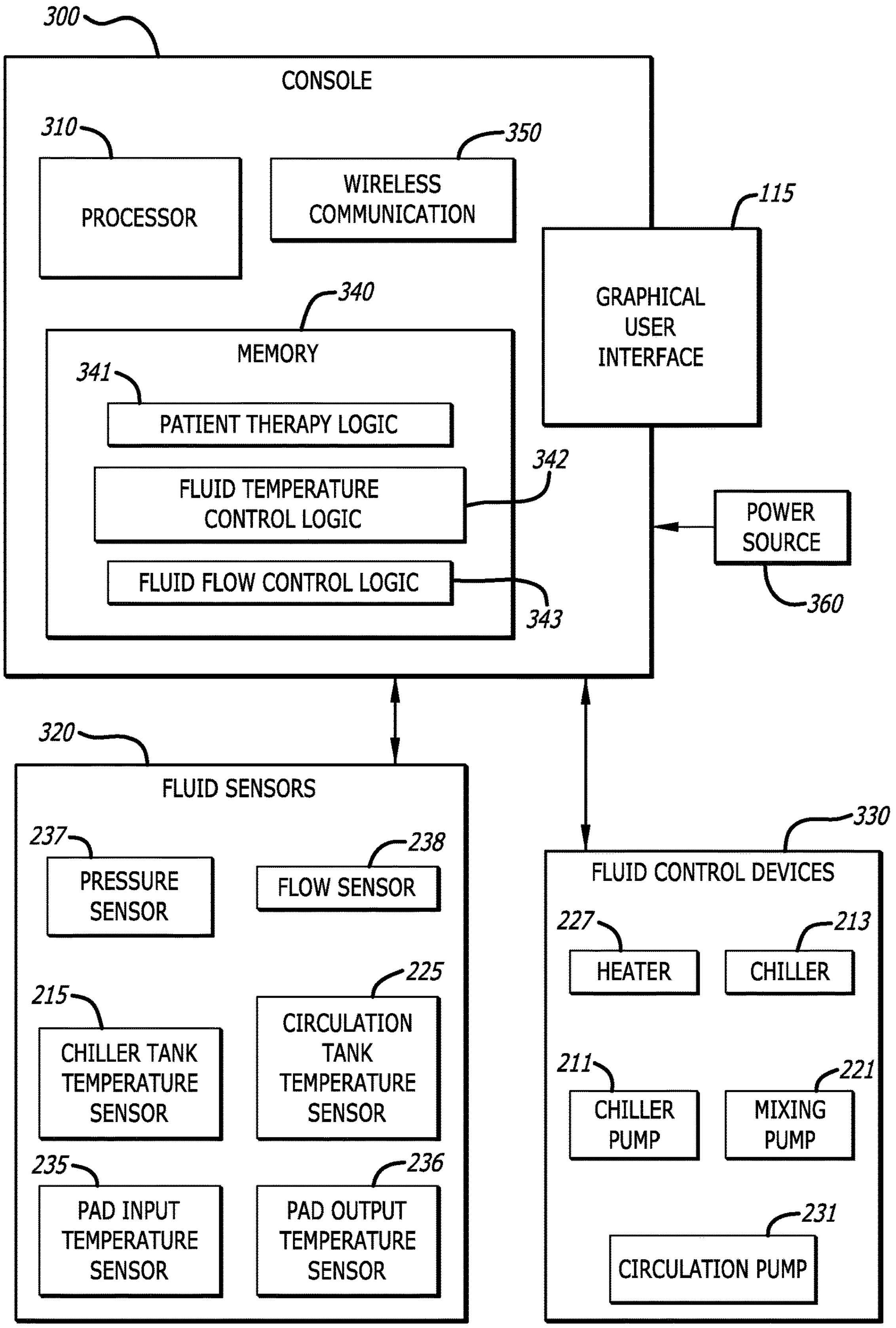
FIG. 3 illustrates a block diagram depicting various elements of a console of the TTM module of FIG. 1, in accordance with some embodiments.

FIG. 3 illustrates a block diagram depicting various elements of the TTM module 110 of FIG. 1, in accordance with some embodiments. The TTM module 110 includes a console 300 including a processor 310 and memory 340 including non-transitory, computer-readable medium. Logic modules stored in the memory 340 include patient therapy logic 341, fluid temperature control logic 342, and fluid flow control logic 343. The logic modules when executed by the processor 310 define the operations and functionality of the TTM Module 110.

Illustrated in the block diagram of FIG. 3 are fluid sensors 320 as described above in relation to FIG. 2. Each of the fluid sensors 320 are coupled to the console 300 so that data from the fluid sensors 320 may be utilized in the performance of TTM module operations. Fluid control devices 330 are also illustrated in FIG. 3 as coupled to the console 300. As such, logic modules may control the operation of the fluid control devices 330 as further described below.

The patient therapy logic 341 may receive input from the clinician via the GUI 115 to establish operating parameters in accordance with a prescribed TTM therapy. Operating parameters may include a target temperature for the TTM fluid 112 and/or a thermal energy exchange rate which may include a time-based target temperature profile. In some embodiments, the fluid temperature control logic 342 may define other fluid temperatures of the TTM fluid 112 within the TTM module 110, such a target temperature for the TTM fluid 112 within the chiller tank 214, for example.

The fluid temperature control logic 342 may perform operations to establish and maintain a temperature of the TTM fluid 112 delivered to the pad 120 in accordance with the predefined target temperature. One temperature control operation may include chilling the TTM fluid 112 within the chiller tank 214. The fluid temperature control logic 342 may utilize temperature data from the chiller tank temperature sensor 215 to control the operation of the chiller 213 to establish and maintain a temperature of the TTM fluid 112 within the chiller tank 214.

Another temperature control operation may include cooling the TTM fluid 112 within the circulation tank 224. The fluid temperature control logic 342 may utilize temperature data from the circulation tank temperature sensor 225 to control the operation of the mixing pump 221 to decrease the temperature of the TTM fluid 112 within the circulation tank 224 by mixing TTM fluid 112 from the chiller tank 214 with TTM fluid 112 within circulation tank 224.

Still another temperature control operation may include warming the TTM fluid 112 within the circulation tank 224. The fluid temperature control logic 342 may utilize temperature data from the circulation tank temperature sensor 225 to control the operation of the heater 227 to increase the temperature of the TTM fluid 112 within the circulation tank 224.

The fluid flow control logic 343 may control the operation of the circulation pump 231. As a thermal energy exchange rate is at least partially defined by the flow rate of the TTM fluid 112 through the pad 120, the fluid flow control logic 343 may, in some embodiments, control the operation of the circulation pump 231 in accordance with a defined thermal energy exchange rate for the TTM therapy.

The console 300 may include or be couple do wireless communication module 350 to facilitate wireless communication with external devices. A power source 360 provides electrical power to the console 300.

Figure 4A:
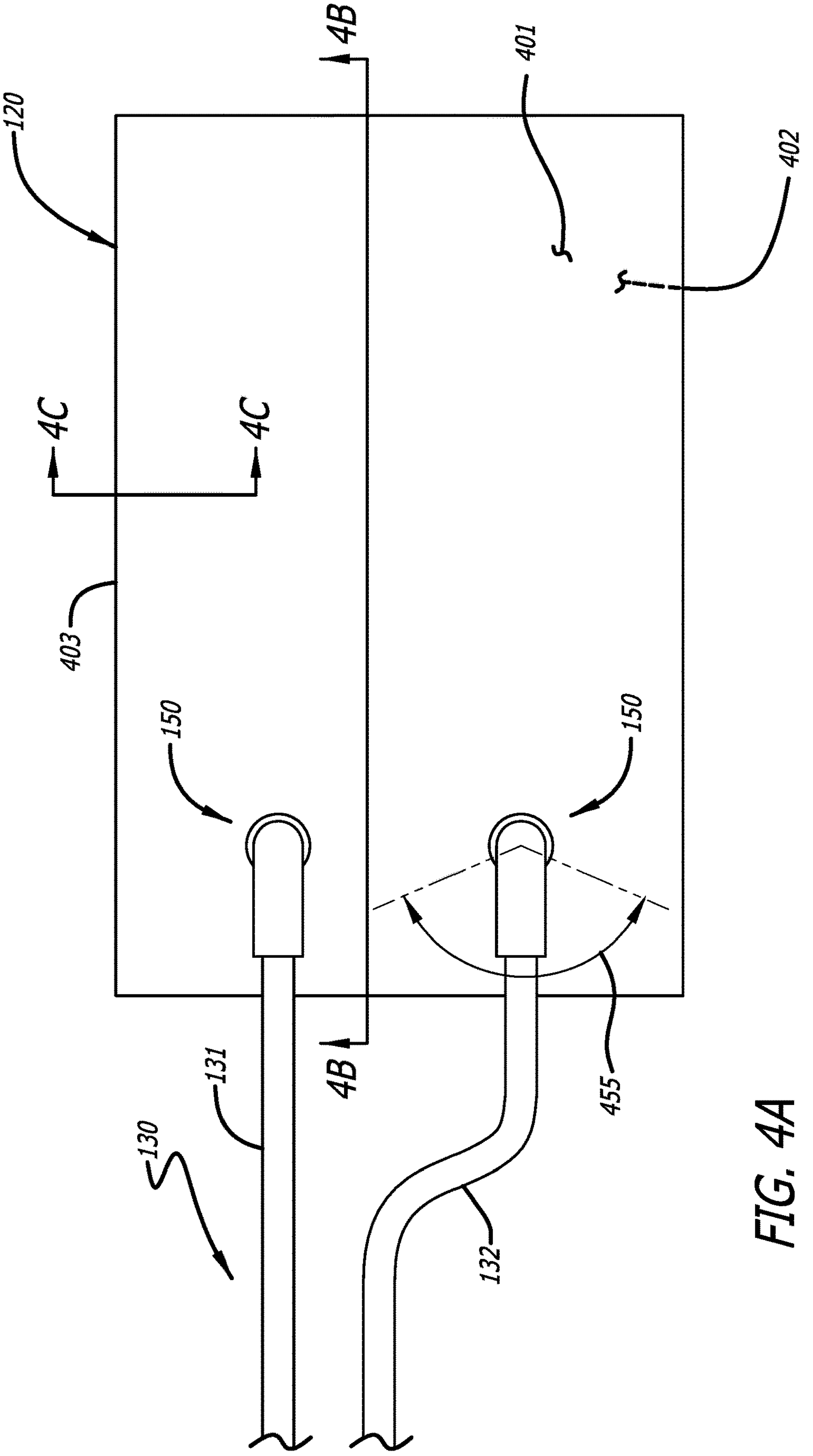
FIG. 4A is a top view of the thermal contact pad of FIG. 1, in accordance with some embodiments.

FIG. 4A shows a top view of the pad 120 in accordance with some embodiments. The pad 120 includes a top surface 401, bottom surface 402, and an outside edge 403 extending along a circumference of the pad 120. In the illustrated embodiment, the pad 120 includes two connector systems 150 coupled to the FDL 130. As illustrated, the connector systems 150 may provide for a rotatable connection between the FDL 130 and the pad 120. The rotatable connection may provide for the FDL 130, or more specifically each of the fluid delivery conduit 131 and the fluid return conduit 132, to rotate through an angle 455 ranging up to about 90 degrees, 180 degrees, or 360 degrees.

Figure 4B:
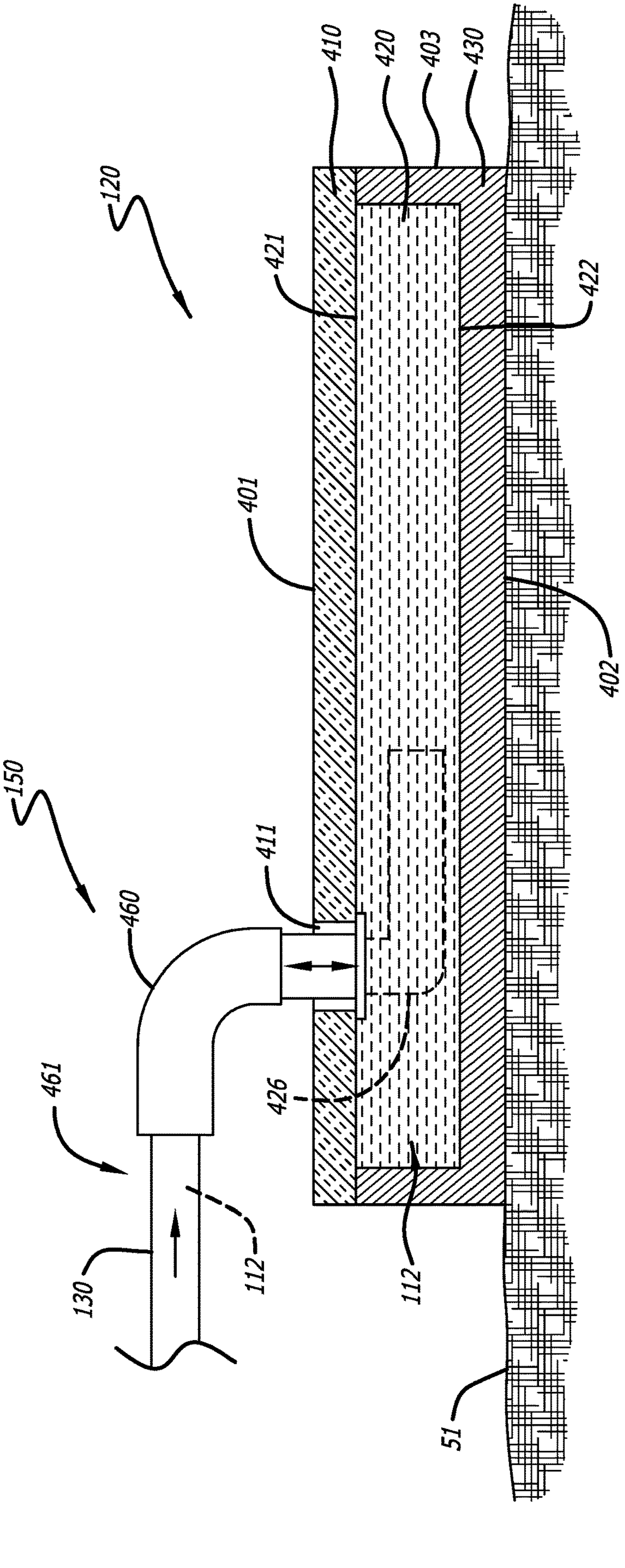
FIG. 4B is a cross-sectional side view of the thermal contact pad of FIG. 4A cut along sectioning lines 4B-4B, in accordance with some embodiments.

FIG. 4B shows a cross-sectional side view of the pad 120 in contact with the skin 51, in accordance with some embodiments. As shown, the connector system 150 may include an elbow 460 to change the direction of FDL 130 extending away from the connector system 150. As shown, the direction of FDL 130 is shifted from a direction perpendicular to the pad 120 to a direction that is substantially parallel to the pad 120. The elbow 450 also establishes an orientation of a distal portion 461 of the FDL 130 to be substantially parallel to the pad 120 and/or the fluid containing layer 420. The fluid containing layer 420 may include one or more internal fluid conduits 426 fluidly coupled to the FDL 130 and the TTM fluid 112 may flow through the internal fluid conduits 426.

The pad 120 includes multiple layers to provide for multiple functions of the pad 120. A fluid containing layer 420 is shown fluidly coupled to the fluid delivery conduit 131 of the FDL 130 to facilitate circulation of the TTM fluid 112 within the fluid containing layer 420. The fluid containing layer 420, having TTM fluid 112 circulating therein, defines a heat sink or a heat source for the patient 50 in accordance with a temperature of the TTM fluid 112. The fluid containing layer 420, or a portion thereof, may be formed of translucent materials so that the fluid containing layer 420, or the portion thereof, is translucent from the top side 421 to the bottom side 422. In other embodiments, the fluid containing layer 420, or a portion thereof, may be formed of transparent materials so that the fluid containing layer 420, or the portion thereof, is transparent from the top side 421 to the bottom side 422.

The pad 120 includes a thermal conduction layer 430 disposed between the fluid containing layer 420 and the patient's skin 51. The thermal conduction layer 430 is configured to facilitate thermal energy exchange between the fluid containing layer 420 and the patient 50. The thermal conduction layer 430 may be attached to the fluid containing layer 420 along a bottom surface 421 of the fluid containing layer 420. The thermal conduction layer 430 may be conformable to provide for intimate thermal contact with the patient 50. In other words, thermal conduction layer 430 may conform to a contour of the patient 50 to facilitate thermal energy exchange between the thermal conduction layer 430 and the patient 50.

The thermal conduction layer 430, or a portion thereof, may be formed of translucent materials so that the thermal conduction layer 430, or the portion thereof, is translucent from the bottom side 422 of the fluid containing layer 420 to the bottom side 402 of the pad 120. In other embodiments, the thermal conduction layer 430, or a portion thereof, may be formed of transparent materials so that the thermal conduction layer 430, or the portion thereof, is transparent from the bottom side 422 of the fluid containing layer 420 to the bottom side 402 of the pad 120.

The pad 120 includes an insulation layer 410 disposed on the top side of the fluid containing layer 420. The insulation layer 410 is configured to inhibit thermal energy transfer between the fluid containing layer 420 and the environment. The insulation layer 410 may be attached to the fluid containing layer 420 along a top surface 422 of the fluid containing layer 420. In some embodiments, the insulation layer 410 may include one or more openings 411 extending through the insulation layer 410 to provide for coupling of the FDL 130 with the fluid containing layer 420.

The insulation layer 410, or a portion thereof, may be formed of translucent materials so that the insulation layer 410, or the portion thereof, is translucent from the top side 401 of the pad 120 to the top side 421 of the fluid containing layer 420. In other embodiments, the insulation layer 410, or a portion thereof, may be formed of transparent materials so that the insulation layer 410, or the portion thereof, is transparent from the top side 401 of the pad 120 to the top side 421 of the fluid containing layer 420.

FIG. 4C is a cross-sectional side view of an embodiment of the pad 120 cut along sectioning lines 4C-4C. In the illustrated embodiment, the pad 120 includes a top chamfer 405 and a bottom chamfer 406 extending along a perimeter of the pad 120. The top chamfer 405 and the bottom chamfer 406 may add flexibility to the pad 120 along the perimeter to reduce pressure contact points and/or abrasion contact points of the pad 120 on the skin 51. As such, the top chamfer 406 and/or the bottom chamfer 405 may inhibit skin irritation of the patient 50 along the perimeter of the pad 120. The top chamfer 406 and/or the bottom chamfer 405 may also allow the clinician to visually observe the skin 51 along the perimeter beneath the pad 120. In some embodiments, the top chamfer 405 and a bottom chamfer 406 may extend around the entire circumference of the pad 120. In other embodiments, the top chamfer 405 and a bottom chamfer 406 may extend along one or more perimeter sections of the circumference. In some embodiments, either one of the top chamfer 405 or the bottom chamfer 406 may be omitted.

FIG. 4D is a cross-sectional side view of another embodiment of the pad 120 cut along sectioning lines 4C-4C. In this illustrated embodiment, the pad 120 includes a rounded perimeter edge 407 of the pad 120. The rounded perimeter edge 407 may include a tube 408 having a wall 409 that is cut lengthwise along a length of the tube 408. The tube 408 may be attached to the pad 120 such that the wall 409 extends around the outside edge 403 of the pad 120 from the top side 401 to the bottom side 402 of the pad 120. The rounded edge 407 may reduce pressure contact points and/or abrasion contact points of the pad 120 on the skin 51. As such, the rounded perimeter edge 407 may inhibit skin irritation of the patient 50 along the rounded perimeter edge 407. In some embodiments, rounded perimeter edge 407 may extend around the entire circumference of the pad 120. In other embodiments, the rounded perimeter edge 407 may extend along one or more perimeter sections of the circumference.

Figure 4E:
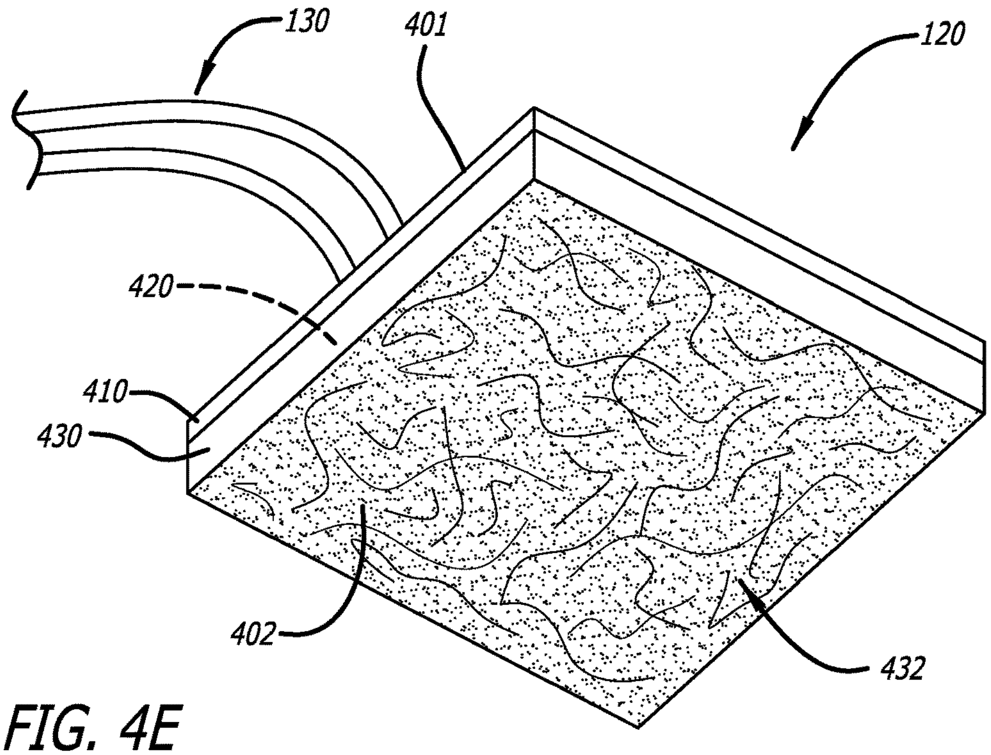
FIG. 4E is a bottom perspective view of thermal contact pad of FIG. 4A illustrating a textured bottom surface, in accordance with some embodiments.

FIG. 4E is a perspective bottom view of the pad 120 showing a textured bottom surface 432 of the thermal conduction layer 430. The textured bottom surface 432 may be configured to provide for breathability of the skin 51 when the pad 120 is applied to the skin 51. The textured bottom surface 432 may facilitate breathability of the skin 51 while maintaining thermal energy exchange between fluid containing layer 420 and the patient 50. The bottom surface 432 may include multiple protrusions and/or depressions that provide for airflow between the skin 51 and the thermal conduction layer 630. The protrusions may include any structure extending away from the surface, such as ribs or bumps, for example. The depressions may include any structure that is depressed from surface such as troughs or dimples, for example. In some embodiments, the textured bottom surface 432 may include a layer component (e.g., a fabric mesh) to provide for breathability of the skin 51.

Figure 5A:
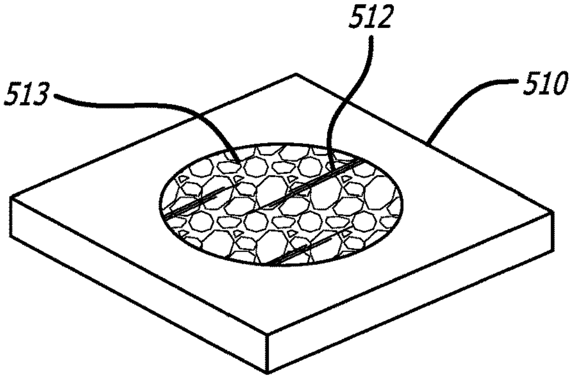
FIG. 5A is a top perspective view of an embodiment of the insulation layer of FIG. 4B, in accordance with some embodiments.

FIG. 5A is a top perspective view of an insulation layer 510 that may be included with the pad 120. The insulation layer 510 can, in certain respects, resemble components of the insulation layer 410. It will be appreciated that all the illustrated embodiments may have analogous features. Relevant disclosure set forth above regarding similarly identified features thus may not be repeated hereafter. However, such features may clearly be the same, or substantially the same, as features depicted in other embodiments and/or described with respect to such embodiments.

The insulation layer 510 includes a translucent portion 512. The translucent portion 512 may be formed of translucent materials and may include multiple air pockets 513 (e.g., enclosed in translucent plastic) that establish thermal insulative properties of the insulation layer 510 while maintaining translucence. In some embodiments, the translucent portion 512 may include the entire insulation layer 510. In other embodiments, the insulation layer 510 may include multiple translucent portions 512. The translucent portion 512 may, in combination with the translucence of the fluid containing layer 420 and the thermal conduction layer 430, provide for visibility of the skin 51 through the pad 120. In other embodiments, the translucent portion 512 may be transparent (e.g., the multiple air pockets 513 enclosed within transparent plastic) so that in combination with the transparency of the fluid containing layer 420 and the thermal conduction layer 430, the pad 120 may provide for transparent visibility of the skin 51 through the pad 120.

Figure 5B:
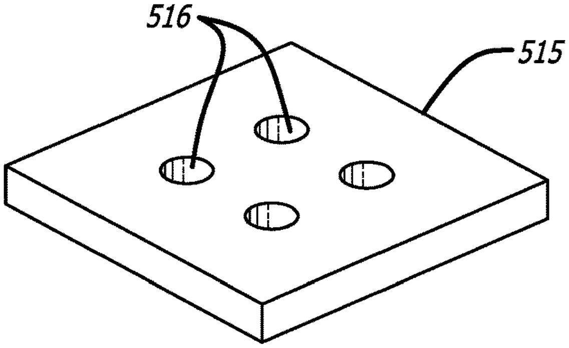
FIG. 5B is a top perspective view of another embodiment of the insulation layer of FIG. 4B, in accordance with some embodiments.

FIG. 5B is a top perspective view of an insulation layer 515 that may be included with the pad 120. The insulation layer 515 includes one or more openings 516 extending through the insulation layer 515. The openings 516 may be configured to provide for visibility through the insulation layer 515. The one or more openings 516 may, in combination with the translucence of the fluid containing layer 420 and the thermal conduction layer 430, provide for visibility of the skin 51 through the pad 120.

By way of summary, in some embodiments, at least a portion of each layer of the pad 120 may be configured for visibility therethrough. In such embodiments, the pad 120 may be formed so that the individual visibility portions of the layers are aligned coincidently with each other. As such, at least a portion of the pad 120 may be configured for translucent and/or transparent visibility therethrough.

Figure 6A:
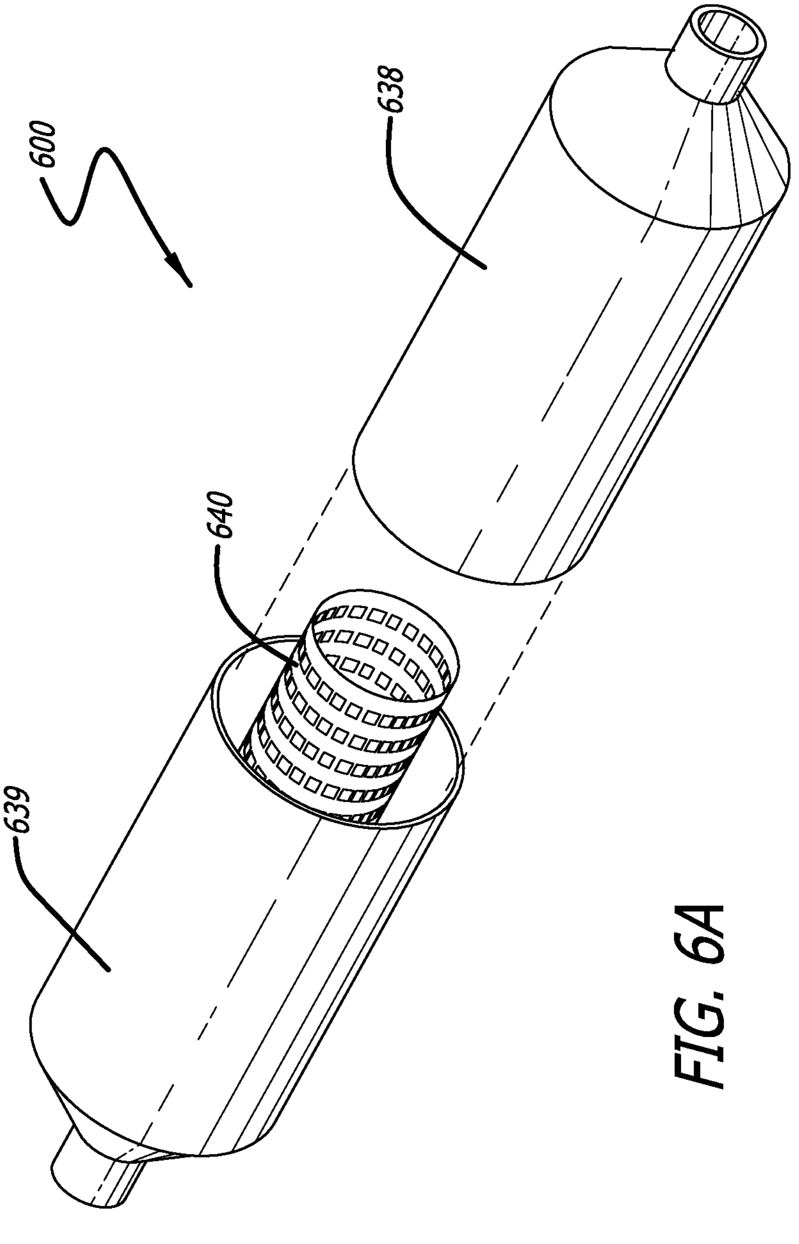
FIG. 6A is an exploded perspective view of a TTM fluid filter, in accordance with some embodiments.
Figure 6B:
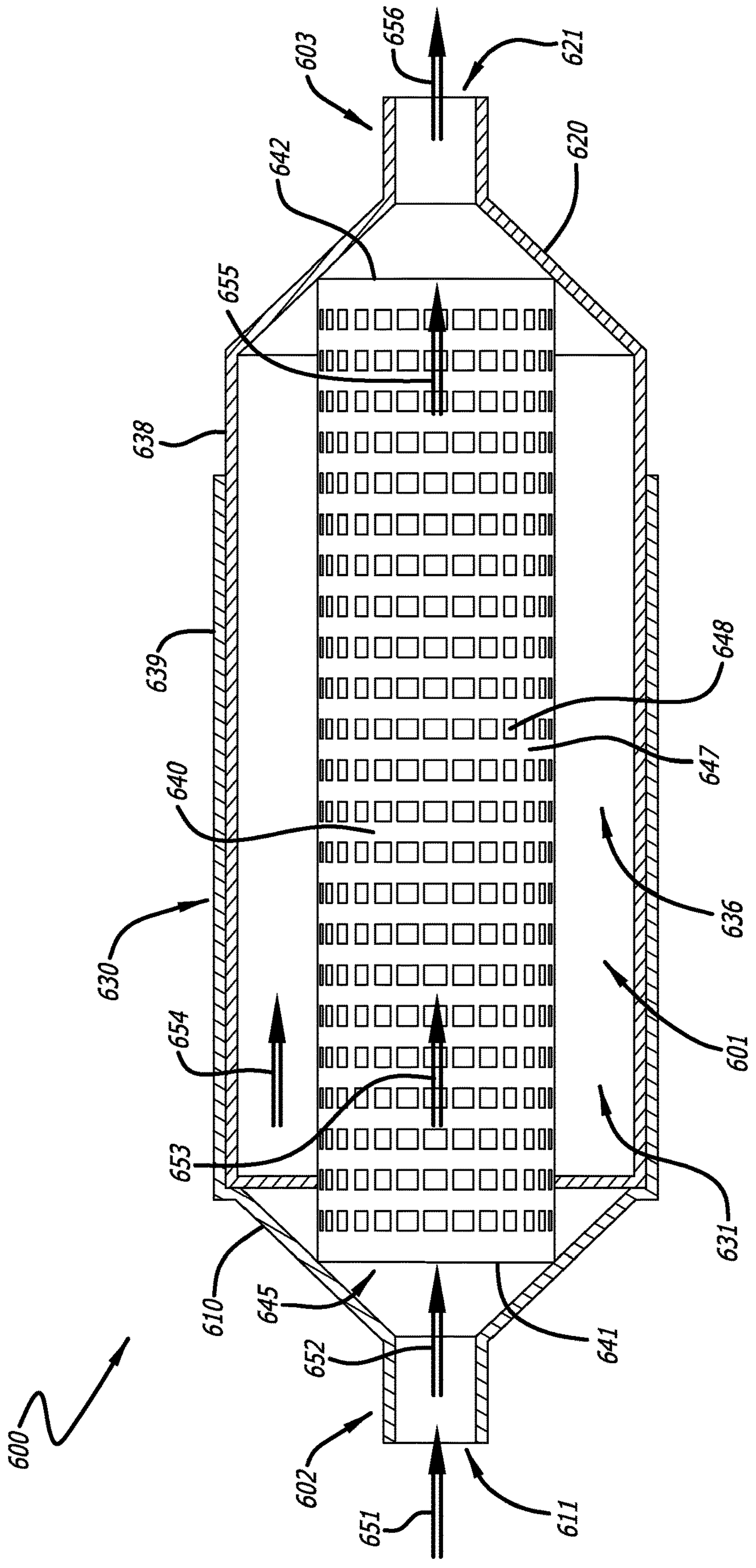
FIG. 6B is a cross-sectional side view of the filter of FIG. 6A, in accordance with some embodiments.

FIGS. 6A and 6B show a filter 600 that may be included with the TTM system 100. The filter 600 may be disposed in line with a TTM fluid flow path of the TTM system 100 so that the circulating TTM fluid 112 flows through the filter 600. The filter 600 may be configured to remove (i.e., filter out) material/particles having a size of 0.2 microns or larger from the TTM fluid 112 without causing a flow restriction of the TTM fluid 112.

The filter 600 includes a longitudinal shape having a flow path 601 extending from a first end 602 to a second end 603. The filter 600 includes a diffuser 610 adjacent the first end 602, a nozzle adjacent 620 the second end 603, and a body 630 extending between the diffuser 610 and the nozzle 620. Along the diffuser 610, a cross-sectional flow area of the filter 600 expands from an inlet flow area 611 to a body flow area 631 and along the nozzle 620, the cross-sectional flow area of the filter 600 contracts from the body flow area 631 to an outlet flow area 621. In some embodiments, the inlet flow area 611 and the outlet flow area 621 may be substantially equal.

In some embodiments, the body flow area 631 may be constant along the body 630. In other embodiments, the body flow area 631 may vary along a length of the body 630 such that the body flow area 631 is greater or less along middle portion of the body 630 than at the ends of the body 630. In some embodiments, the body flow area 631 may be circular.

The filter 600 includes an inner tube 640 disposed within the body 630 extending along the length of body 630. The inner tube 640 may be coupled to the diffuser 610 at a first inner tube end 641 so that TTM fluid 112 entering the filter 600 at the first end 602 also enters the inner tube 640 at the first inner tube end 641. The inner tube 640 may be coupled to the nozzle 620 at a second inner tube end 642 so that TTM fluid 112 exiting the filter 600 at the second end 603 also exits the inner tube 640 at the second inner tube end 642.

The inner tube 640 includes an inner tube flow area 645 extending the length of the inner tube 640. The inner tube flow area 645 may be greater than the inlet flow area 611 and/or the outlet flow area 621. The inner tube flow area 645 may be constant along the length of the inner tube 640. In some embodiments, the inner tube flow area 645 may vary along the length of the inner tube 640. In some embodiments, the inner tube 640 may include a circular cross section. The inner tube 640 and the body 630 may be configured so that the body flow area 631 includes a combination of the inner tube flow area 645 and an annular flow area 636.

The inner tube 640 includes a porous a circumferential wall 647. The porous wall 647 may be configured so that TTM fluid 112 may flow through the porous wall 647, i.e., through the pores 648 of the porous wall 647. Consequently, TTM fluid 112 may flow through the porous wall 647 from the inner tube flow area 645 to the annular flow area 636 and from the annular flow area 636 into the inner tube flow area 645.

In use, the longitudinal velocity of the TTM fluid 112 may change along the length of the filter 600. As the volumetric TTM fluid 112 flow through the filter is constant, the longitudinal velocity of the TTM fluid 112 may be at least partially defined by the flow areas of the filter 600 as described below. The TTM fluid 112 may enter the filter 600 at a first longitudinal velocity 651 and decrease along the diffuser so that the TTM fluid 112 enters the inner tube at a second velocity 652 less than the first longitudinal velocity 651. At this point, a portion of the TTM fluid 112 may flow through the porous wall 647 from the inner tube flow area 645 into the annular flow area 636 to divide the fluid flow into a third velocity 653 within the inner tube flow area 645 and a fourth velocity 654 within the annular flow area 636. The fourth velocity 654 may be less than the third velocity 653. A portion of the TTM fluid 112 may then flow back into the inner tube flow area 645 from the annular flow area 636 to define a fifth velocity 655 along the inner tube flow area 645 which may be about equal to the second velocity 652. The TTM fluid 112 may then proceed along the nozzle 620 to define a sixth velocity 656 exiting the filter 600. In some embodiments, the first velocity 651 and the sixth velocity 656 may be about equal.

The filter 600 may be configured to remove harmful bacteria and viruses from the TTM fluid 112 using sedimentation principles. In use, the filter 600 may be oriented horizontally so that the direction of fluid flow through the filter 600 is perpendicular to a gravitational force 665. In some instances, bacteria, viruses, and other particles within the TTM fluid 112 may have a greater density than the TTM fluid 112 and as such may be urged by the gravitational force 665 (i.e., sink) in a direction perpendicular to the fluid flow direction. In some instances, particles within the inner tube flow area 645 may sink toward and through the porous wall 647 into the annular flow area 636. Particles within the annular flow area 636 may then sink toward an inside surface 631 of the body 630 and become trapped adjacent the inside surface 631. The geometry of the filter 600 may be configured to allow 0.2-micron bacteria/virus particles to fall out of the flow of TTM fluid 112 and become trapped along the inside surface 631.

In some embodiments, the filter 600 may be configured so that flow of TTM fluid 112 from the inner tube flow area 645 into the annual flow area 636 may drag particles through the porous wall 647. In some embodiments, the inlet flow area 611, the inner tube flow area 645, and the annual flow area 636 may be sized so that the third velocity 1053 is less than about 50 percent, 25 percent, or 10 percent of the first velocity 651 or less. In some embodiments, the body 630 and the inner tube 640 may be configured so that the fourth velocity 654 is less than the third velocity 653. In some embodiments, the fourth velocity 654 may less than about 50 percent, 25 percent, or 10 percent of the third velocity 653 or less.

In some embodiments, the filter 600 may be configured so that the flow within the inner tube flow area 645 is laminar flow, i.e., so that the velocity of the fluid flow adjacent to or in close proximity to an inside surface 641 of the porous wall 647 is less than the velocity at a location spaced away from the inside surface 641. In such an embodiment, the particles may more readily sink toward and through the porous wall 647.

In some embodiments, the filter 600 may be configured so that the fluid flow within the annual flow area 636 is laminar flow, i.e., so that the velocity of the fluid flow adjacent to or in close proximity to inside surface 631 of the body 630 is less than the velocity at a location spaced away from the inside surface 631. In such an embodiment, the particles may more readily sink toward and be trapped along the inside surface 631.

The filter 600 may include three components including the inner tube 640 an inner body shell 638, and an outer body shell 639. Each of the three components may be formed via the plastic injection molding process. Assembly of the filter 600 may include capturing the inner tube 640 within the inner body shell 638 and the outer body shell 639 and sliding the inner body shell 638 into the outer body shell 639 wherein the fit between the inner body shell 638 and the outer body shell 639 is an interference fit.

Figure 6C:
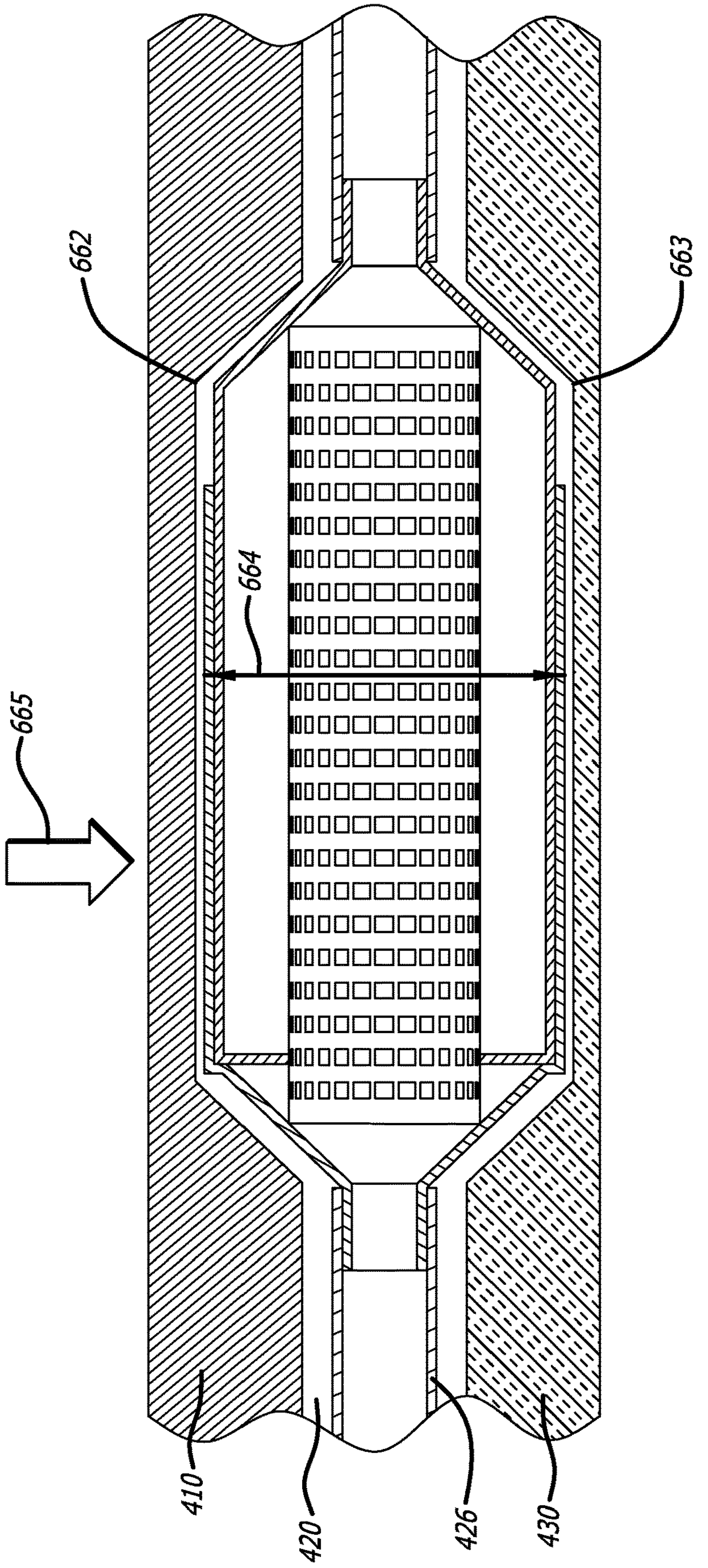
FIG. 6C is a side cross-sectional view of the thermal contact pad of FIG. 1 incorporating the filter of FIG. 6A, in accordance with some embodiments.

In some embodiments, the filter 600 may be disposed within the pad 120. FIG. 6C shows a detail cross-sectional view of the pad 120 including the filter 600 disposed within the fluid containing layer 420. The filter 600 is coupled in line with the internal fluid conduit 426 within the fluid containing layer 420 so that TTM fluid 12 circulating within the pad 120 passes through the filter 600. The filter 600 may be sized so that the inlet flow area 611 and the outlet flow area 621 are similar to a cross-sectional flow area of the internal flow path 660 within the fluid containing layer 420.

In some embodiments, a thickness of the fluid containing layer 420 may increase adjacent the filter 600 to accommodate a body diameter 664 of the filter 600. To further accommodate the body diameter 664, the insulation layer 410 and/or the thermal conduction layer 430 may include internal depressions 662, 663, respectively.

In some embodiments, one or more filters 600 may be disposed in line with the flow of TTM fluid 112 at other locations of the TTM system 100. In some embodiments, one or more filters 600 may be disposed within the TTM module 110. In some embodiments, one or more filters 600 may be disposed in line with the FDL 130. In some embodiments, the filter 600 may be disposed in line with a fluid conduit of the pad external to the fluid containing layer 420 such as a conduit extending between the pad connector 652 and the pad 120.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A method of providing a targeted temperature management (TTM) therapy to a patient, comprising:
providing a TTM system comprising:
a TTM module configured to provide a TTM fluid;
a thermal pad configured to receive the TTM fluid from the TTM module to facilitate thermal energy transfer between the TTM fluid and the patient; and
a fluid delivery line (FDL) extending between the TTM module and the thermal pad, the FDL configured to provide TTM fluid flow between the TTM module and the thermal pad,
wherein the thermal pad comprises:
a top side and a bottom side,
a fluid containing layer disposed between the top side and the bottom side,
wherein
the fluid containing layer is configured for containing the TTM fluid,
the fluid containing layer comprises a fluid inlet and a fluid outlet, and
the TTM fluid is circulatable within the fluid containing layer from the fluid inlet to the fluid outlet;
an insulation layer disposed on the top side; and
a thermal conduction layer disposed on the bottom side;
applying the thermal pad to a skin of the patient;
delivering the TTM fluid from the TTM module to the thermal pad; and
visually observing the skin through a translucent portion of the thermal pad, wherein one or more openings extending through the insulation layer enable visual observation of the skin through the translucent portion.

2. The method according to claim 1, further comprising passing the TTM fluid through a filter coupled to the fluid containing layer.

3. The method according to claim 1, wherein the thermal pad further comprises a chamfered edge extending along a perimeter of the thermal pad.

4. The method according to claim 1, wherein the thermal pad further comprises a rounded edge extending along a perimeter of the thermal pad.

5. The method according to claim 1, wherein the thermal conduction layer comprises a textured bottom surface to facilitate breathability of the skin beneath the thermal pad.

* * * * *